US011760636B2

(12) United States Patent
Ramsurn et al.

(10) Patent No.: US 11,760,636 B2
(45) Date of Patent: Sep. 19, 2023

(54) VACUUM-FREE, HYDROGEN-FREE CATALYTIC SYNTHESIS OF GRAPHENE FROM SOLID HYDROCARBONS

(71) Applicant: THE UNIVERSITY OF TULSA, Tulsa, OK (US)

(72) Inventors: Hema Ramsurn, Tulsa, OK (US); Rahul Kundu, Tulsa, OK (US)

(73) Assignee: The University of Tulsa, Tulsa, OK (US)

(*) Notice: Subject to any disclaimer, the term of this patent is extended or adjusted under 35 U.S.C. 154(b) by 0 days.

(21) Appl. No.: 17/286,917

(22) PCT Filed: Oct. 24, 2019

(86) PCT No.: PCT/US2019/057850
§ 371 (c)(1),
(2) Date: Apr. 20, 2021

(87) PCT Pub. No.: WO2020/086841
PCT Pub. Date: Apr. 30, 2020

(65) Prior Publication Data
US 2021/0309523 A1    Oct. 7, 2021

Related U.S. Application Data

(60) Provisional application No. 62/751,313, filed on Oct. 26, 2018.

(51) Int. Cl.
*C01B 32/184*    (2017.01)
*C07C 27/06*    (2006.01)
(Continued)

(52) U.S. Cl.
CPC .......... *C01B 32/184* (2017.08); *C07C 27/06* (2013.01); *C23C 16/26* (2013.01); *B82Y 30/00* (2013.01); *B82Y 40/00* (2013.01)

(58) Field of Classification Search
None
See application file for complete search history.

(56) References Cited

U.S. PATENT DOCUMENTS 1,497,543 A * 6/1924 Chaney ................. C01B 32/336
  502/433
4,552,863 A * 11/1985 Fujimori ............... C01B 32/384
  264/29.3
(Continued)

FOREIGN PATENT DOCUMENTS

CN    103708440    * 4/2014    ............. C01B 32/05
CN    105036123    11/2015
(Continued)

OTHER PUBLICATIONS

Kambo et al. "Comarative evaluation of torrefaction and hydrothermal carbonization of lignocellulosic biomass for the production of solid biofuel" Energy Conv. and Mgt 105 2015 746-755 (Year: 2015).*

(Continued)

*Primary Examiner* — Mandy C Louie
(74) *Attorney, Agent, or Firm* — McAfee & Taft

(57) ABSTRACT

Disclosed is a process for producing graphene from solid hydrocarbons including biomass and coal. The disclosed method does not require the presence of hydrogen and does not operate under a vacuum. The method begins by converting biomass to a graphene precursor while coal is used as is. Subsequently, the method grinds the graphene precursor to provide a desired particle size. The particles of graphene precursor (biocoal or coal) are converted to graphene by catalytic conversion on metallic foil under atmospheric conditions and in the absence of hydrogen.

37 Claims, 20 Drawing Sheets

(51) Int. Cl.
*C23C 16/26* (2006.01)
*B82Y 30/00* (2011.01)
*B82Y 40/00* (2011.01)

(56) References Cited

U.S. PATENT DOCUMENTS

| | | | | |
|---|---|---|---|---|
| 8,884,310 | B2* | 11/2014 | Seacrist | H01L 29/06 |
| | | | | 257/77 |
| 9,187,332 | B2 | 11/2015 | Yoon et al. | |
| 9,540,244 | B2 | 1/2017 | Zhang et al. | |
| 10,213,985 | B2 | 2/2019 | Kim et al. | |
| 10,269,505 | B2 | 4/2019 | Lee et al. | |
| 2013/0164812 | A1* | 6/2013 | Nicholas | C12M 35/02 |
| | | | | 435/283.1 |
| 2014/0001026 | A1* | 1/2014 | Baird | C10B 49/22 |
| | | | | 201/2 |
| 2014/0170317 | A1* | 6/2014 | Li | C23C 16/26 |
| | | | | 427/249.6 |
| 2014/0234200 | A1* | 8/2014 | Tour | C01B 32/194 |
| | | | | 423/448 |
| 2014/0328006 | A1 | 11/2014 | Mitlin et al. | |
| 2015/0144831 | A1* | 5/2015 | Mennell | B01J 20/02 |
| | | | | 252/62.55 |
| 2016/0060122 | A1 | 3/2016 | Tour et al. | |
| 2016/0101980 | A1 | 4/2016 | Hasegawa et al. | |
| 2016/0289150 | A1* | 10/2016 | Delgass | C07D 307/46 |
| 2017/0037333 | A1 | 2/2017 | Mennell et al. | |
| 2017/0051078 | A1* | 2/2017 | Tang | C01B 32/184 |
| 2017/0113936 | A1* | 4/2017 | Zhang | B01J 23/745 |
| 2018/0194630 | A1 | 7/2018 | Cai et al. | |
| 2019/0003042 | A1* | 1/2019 | Seo | C23C 16/4485 |
| 2019/0074142 | A1 | 3/2019 | Gartia et al. | |
| 2020/0261858 | A1* | 8/2020 | Seo | C01B 32/186 |

FOREIGN PATENT DOCUMENTS

| | | | | |
|---|---|---|---|---|
| CN | 106348274 | * | 1/2017 | ......... C01B 2204/04 |
| WO | 2016130026 | | 8/2016 | |

OTHER PUBLICATIONS

Liu, Y, et al., Design and Preparation of Biomass-Derived Carbon Materials for Supercapacitors: A Review, Journal of Carbon Research, vol. 4(53), DOI: 10.3390/c4040053, pp. 7, 18, 20, tables 2, 8 Sep. 25, 2018.

Shah, J., et al., Plasma Synthesis of Graphene from Mango Peel, ACS Omega, vol. 3, DOI: 10.1021/acsomega.7b01825, pp. 457, 461 Jan. 16, 2018.

Krotz, L., et al, Elemental Analysis: CHNS/O Characterization of Biomass and Bio-Fuels, p. 4, table 4 2017.

PCT International Search Report and Written Opinion received in corresponding PCT Application No. PCT/US2019/057850 dated Mar. 12, 2020, pp. 1-13.

Prabhas, Jana, et al., Co-production of graphene sheets and hydrogen by decomposition of methane using cobalt based catalysts, Energy & Environmental Science, 2011, vol. 4, DOI: 10.1039/c0ee00490a, pp. 778-783.

Das, Vijay Kumar, et al., Graphene and graphene-like materials in biomass conversion: paving the way to the future, Journal of Materials Chemistry A, DOI: 10.1039/c7ta09418c, 2017, 5, 25131-25143.

Information Disclosure Statement filed in U.S. Appl. No. 15/400,281, dated Jun. 8, 2017, pp. 1-11.

* cited by examiner

XRD analysis of Fe foil and Fe foil after annealing at 700, 800, 900 and 1000°C with cellulose graphene precursor XRD analysis of Fe foil and Fe foil after annealing at 700, 800, 900 and 1000°C with lignin graphene precursor XRD analysis of Co foil and Co foil after annealing at 800, 900 and 1000°C with cellulose graphene precursor.

XRD analysis of Co foil and Co foil after annealing at 800, 900 and 1000°C with lignin graphene precursor.

VACUUM-FREE, HYDROGEN-FREE CATALYTIC SYNTHESIS OF GRAPHENE FROM SOLID HYDROCARBONS

BACKGROUND

Graphene was originally produced in pure form in 2004 by mechanical peeling of graphite by Novoselov, K. S. et al. Graphene consists of one atom thick $sp^2$ hybridized carbon atoms arranged hexagonally and it has been a great area of interest since its discovery in 2004 due to its electronic and physical properties. Graphene is basically a layer of graphite that is known to exhibit low temperature mobilities up to 200000 $cm^2V^{-1}$ $s^{-1}$, fractional quantum hall effect, and known to absorb 2.3% of visible light. The work on converting carbonaceous material to graphitic material started back in 1865 where graphite was prepared from powdered coke.

SUMMARY

Disclosed is a method for producing a graphene from solid hydrocarbons such as coal, biocoal or biochar. When using biocoal or biochar as the precursor to graphene the method provides for carbonization of biomass in the presence of water at a ratio of about 1:5 to about 1:10. The resulting graphene precursor is placed on a metal foil. The foil with the graphene precursor on its surface is placed in a reactor located in a furnace or other heating apparatus. The furnace is heated to a temperature between about 750° C. to about 1200° C. for a period of about 30 minutes to two hours. Following heating, the furnace is cooled at a rate of about 1° C./min to about 100° C./min to a temperature between about 400° C. and 800° C. Subsequently, the reactor is exposed to ambient temperatures and allowed to cool to room temperature. During the cooling process graphene forms on the surface of the metal foil.

Disclosed is a method for preparing a graphene precursor. The method includes the steps of: providing a plant based source of carbon, said plant based source containing at least 20% carbon by weight; mixing said plant based source of carbon with water at a ratio of about one part plant based source of carbon to five parts water to about one part plant based source of carbon to ten parts water to form a mixture of plant based source of carbon in water; carbonizing the plant based source of carbon in water by heating the mixture of plant based source of carbon in water to a temperature between about 200° C. and about 400° C. for a period of at least 30 minutes; and, isolating the graphene precursor.

Also disclosed is a method for preparing graphene from a graphene precursor. The method of preparing graphene includes the steps of: providing a graphene precursor having carbon, oxygen and hydrogen weight percentages in the following ranges: C: 40-95%, O: 15-50%, Hydrogen: 3-10%; dry the graphene precursor at a temperature between about 100° C. and about 110° C. for a period of about 12 hours to about 24 hours; reducing the particle size of the graphene precursor; placing the graphene precursor on a metal foil and placing the metal foil with the graphene precursor on its surface in a reactor; flowing a gas that is non-reactive with the graphene precursor through the reactor; increasing the temperature of the reactor to a first target temperature between about 750° C. and about 1200° C.; maintaining the target temperature for about 30 minutes to about 120 minutes; cooling the reactor to a second target temperature between about 400° C. and about 800° C.; cooling the reactor to ambient conditions; thereby providing layered graphene on surface of the metal foil.

DETAILED DESCRIPTION

Figure 1:
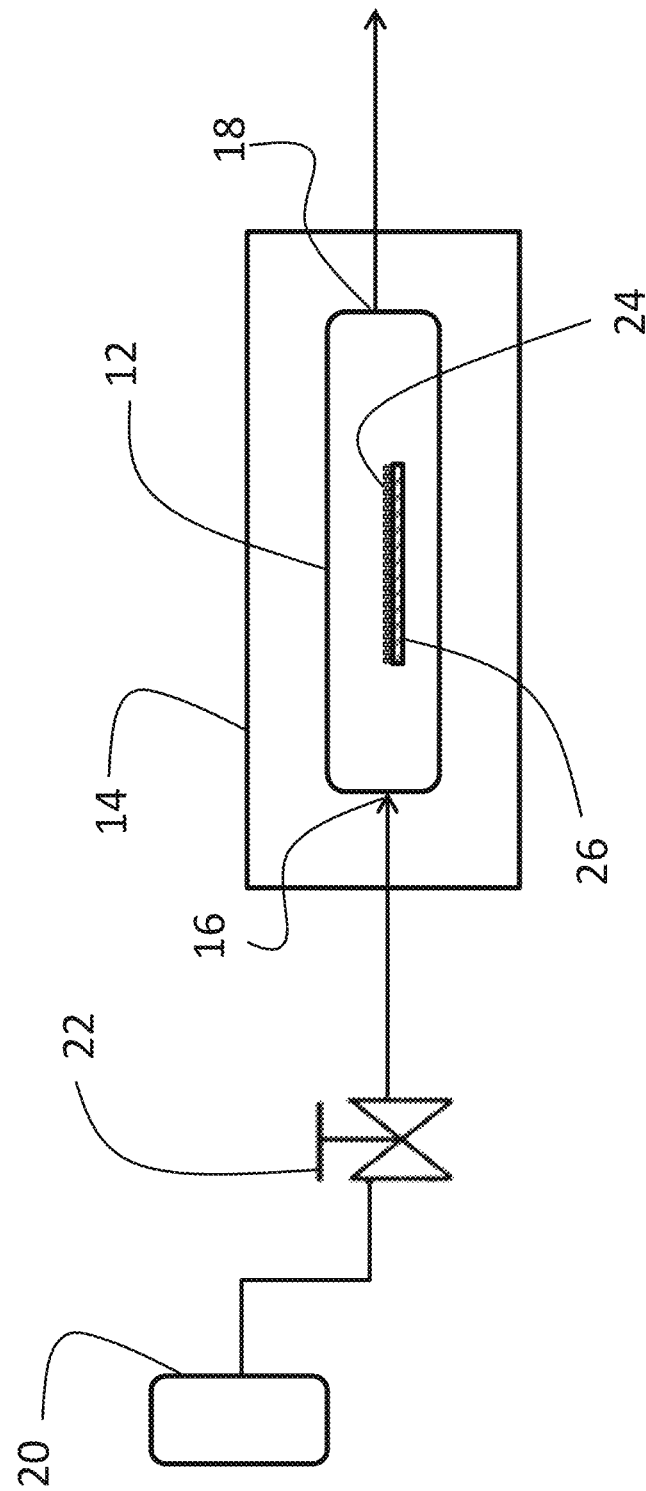
FIG. 1 is a schematic of a reactor suitable for carrying out the disclosed process.

The following discussion describes methods for producing graphene on a metal foil surface. The described methods do not require the use of a vacuum or the presence of hydrogen. Rather, the final step of producing graphene takes place under a generally inert atmosphere at a pressure of approximately one atmosphere. As used herein, the term inert atmosphere means that the atmosphere under which the conversion to graphene occurs does not take part in the associated reaction steps. As defined by the International Standards Organization (ISO), graphene is a layer of $sp^2$ carbon atoms. Three to nine stacked layers of these $sp^2$ carbon atoms is called "few-layer graphene." Ten or more stacked layers are called graphite. For the purposes of this disclosure, the term graphene precursor is considered generic to biochar, biocoal and coal.

In one embodiment, a hydrothermal carbonization method of producing the graphene precursor uses biomass as the raw material. Biomass refers to plant matter and may include model compounds like cellulose, hemicellulose and lignin as well as biodegradable, agriculture and forests wastes, or algae. Common plant sources of biomass include, but are not limited to, *miscanthus*, switchgrass, hemp, corn, poplar, willow, sugarcane. In general, the biomass material will contain at least 20% carbon by weight. Subsequently, the biomass is mixed with water and carbonized by heating in a reactor by a furnace or other conventional heating apparatus. The reaction temperature is about 200° C. to about 400° C. Thus, the biomass is heated to a temperature of about 200° C. to about 400° C. as monitored by a thermocouple or other convenient temperature monitoring device. Typically, the ratio of biomass to water, by weight, during the carbonization step will be from about 1:5 to about 1:10 (biomass:water). For example, on a lab scale one gram of biomass will be carbonized in the presence 5 g to 10 g of water.

During the carbonization step, the biomass/water combination is placed in the reactor and the temperature within the reactor increased from room temperature to the target temperature at a rate of about 5° C./minute to about 10° C./minute. Upon reaching the target temperature between about 200° C. and about 400° C., operational conditions are maintained for a period of at least 30 minutes. More preferably, the target temperature will be between about 250° C. and about 300° C. Because the reactor is sealed, vaporization of water under these conditions will increase pressure within the reactor. Thus, the carbonization takes place in the presence of water at pressures greater than atmospheric pressure. Typically, the carbonization step takes place under a pressure of about 2 MPa to about 20 MPa. More commonly, the pressure of carbonization will be between about 5 MPa and about 15 MPa. Following the carbonization step, the biomass has been converted to a graphene precursor.

A suitable graphene precursor for conversion to graphene according to the following graphene conversion method will have mass weight percentages of carbon, oxygen and hydrogen in the following ranges: C: 40-95%, O: 15-50%, Hydrogen: 3-10%. More typically, suitable graphene precursor will have mass weight percentages of carbon, oxygen and hydrogen in the following ranges: C: 40-70%, O: 15-50%, Hydrogen: 4-10%.

A typical cellulose based graphene precursor prepared by hydrothermal carbonization will have mass weight percentages of carbon, oxygen and hydrogen in the following ranges: C: 50-70%, O: 25-36.5%, Hydrogen: 4-6%. A typical lignin based graphene precursor prepared by hydrothermal carbonization will have mass weight percentages of carbon, oxygen and hydrogen in the following ranges: C: 50-60%, O: 30-35%, Hydrogen: 4-%.

Graphene precursors which do not require carbonization prior to use as a graphene precursors in the following method include: peat, lignite coal, bituminous coal and anthracite coal. Peat suitable for use as graphene precursor will have mass weight percentages of carbon, oxygen and hydrogen in the following ranges: C: 55-60%, O: 30-35%, Hydrogen: 6-6.5%. Lignite coal suitable as a graphene precursor will have mass weight percentages of carbon, oxygen and hydrogen in the following ranges: C: 65-70%, O: 20-25%, Hydrogen: 4-5%. Bituminous coal based graphene precursors will have mass weight percentages of carbon, oxygen and hydrogen in the following ranges: C: 75-85%, O: 5-10%, Hydrogen: 4-5%. Anthracite coal based graphene precursors will have mass weight percentages of carbon, oxygen and hydrogen in the following ranges: C: 90-95%, O: 2-4%, Hydrogen: 3-4%.

Additionally, graphene precursors may be prepared from biomass using known torrefaction methods. For example, wood chips may be converted to a graphene precursor through the torrefaction process. Such graphene precursors will have mass weight percentages of carbon, oxygen and hydrogen in the following ranges: C: 50-70%, O: 20-45%, Hydrogen: 4-7%.

The examples discussed below utilized a graphene precursor prepared from a cellulose biomass and a graphene precursor prepared from a lignin biomass by hydrothermal carbonization. The cellulose graphene precursor was determined to have: C=68.93%, H=5.08%, O=24.64%, N=0.11%, S=1.24%. The lignin graphene precursor was determined to have: C=58.95%, H=5.07%, O=33.76%, N=0.25%, S=1.97%. In the examples below, analysis of the biomass and its graphene precursor after the carbonization step shows a decrease in the oxygen to carbon (0/C) ratios. In the case of the cellulose biomass the 0/C=0.8 while the graphene precursor 0/C=0.27 and in the case of lignin biomass the 0/C=0.57 to while the graphene precursor 0/C=0.42. In general, the conversion of biomass to graphene precursor will result in a decrease of the 0/C ratio where the ratio of 0/C of produced graphene precursor is about 0.2 to 0.45. This decrease in 0/C ratio is due to loss of oxygen containing functional groups in the graphene precursor.

Following the preparation of the graphene precursor, the method provides an optional step of removing the bio-oils formed during the carbonization step. These bio-oils consist primarily of phenolic and furanic compounds and make up about 5% to 20% by weight of the graphene precursor. The presence of the bio-oils during the subsequent heating step will foul the reactor and may interfere with the conversion of the graphene precursor to graphene reducing the overall yield of graphene. Therefore, the removal of the bio-oils will typically be carried out. The bio-oil removal step utilizes an organic solvent such as acetone, methyl ethyl ketone, tetrahydrofuran and other similar organic solvents suitable for solubilizing the bio-oils. The bio-oil removal step utilizes a sufficient amount of solvent to remove the bio-oils. Typically, about 75 ml to 100 ml of the organic solvent per gram of graphene precursor will provide substantially complete removal of bio-oils present in the graphene precursor.

A second optional step that may be carried out on the graphene precursor prior to the catalytic formation of graphene is an acid wash. The graphene precursor may include inorganic materials at weight percentages of up to 40% by weight. Therefore, an optional acid wash step may be used to substantially remove all inorganic materials from the graphene precursor. Typically, the acid wash step will use an acid such as 0.1 N nitric acid or 0.1 N sulfuric acid. To ensure substantially complete removal of the inorganic materials, the acid wash takes place over about 12 hours to about 24 hours at a temperature between about 90° C. and about 100° C. and atmospheric pressure. Typically, the acid wash step will use from about 50 ml of acid per gram of graphene precursor to about 150 ml of acid per gram of graphene precursor. Upon completion of the acid wash, the graphene precursor is neutralized by washing with water at a temperature between about 20° C. and about 25° C. for about 5 minutes to about 10 minutes.

Following the optional removal of oils and acid washing steps and neutralization, the graphene precursor is dried at a temperature of about 100° C. to about 110° C. for about 12 hours to about 24 hours. After drying, the graphene precursor is reduced by any conventional process to a particle size corresponding to about 35 U.S. Standard mesh. Generally, the particle size will correspond to about 80 U.S. standard mesh or smaller particles. More typically, the particle size will correspond to about 100 U.S. standard mesh or smaller particles. Preferably, the particle size is 80 U.S. Standard Mesh and smaller. Typically, a grinding process will provide the desired sizing of the graphene precursor.

Following sizing, the graphene precursor is ready for catalytic conversion to graphene. The catalytic step takes place under an inert atmosphere within a furnace or other suitable heating device. In one embodiment, the conversion process occurs within a reactor formed from a material that is non-reactive with the components within the reactor. One suitable reactor is depicted in FIG. 1 as a quartz tube 12 located in a furnace 14. Quartz tube 12 is provided with suitable gas inlets 16 and outlets 18 to provide for a flowing stream of a gas from a source 20. A valve 22 controls the flow of the gas. The gas typically flows at 20-100 ml/hour (Space Velocity: 0.052-0.263 $h^{-1}$) that is non-reactive with the graphene precursor during the catalytic process. As depicted in FIG. 1, the graphene precursor 24 is positioned on a metal foil 26. The flowing gas maintains the reaction chamber under near atmospheric pressure conditions, i.e. within 1 psi of atmospheric pressure, and precludes reaction of the graphene precursor with oxygen. Additionally, the volume and flow rate of the flowing gas is sufficient to remove substantially all atmospheric oxygen from the reaction chamber and to sweep out any gases that may evolve during the conversion of the graphene precursor to graphene. In general, the flowing gas maintains the reaction chamber at or close to atmospheric pressure. Suitable gases for use in the catalytic step include nitrogen, argon, helium and any other gas that is non-reactive with the graphene precursor under the operational conditions within the furnace. Thus, the graphene conversion step occurs in the absence of oxygen and hydrogen and at near atmospheric conditions. Thus, the disclosed method does not require a reaction chamber capable of operating under a vacuum or at high atmospheric pressures. Additionally, the graphene conversion step will take place in the absence of hydrogen (unlike the conventional chemical vapor deposition (CVD) method, which requires the presence of hydrogen). Thus, the process disclosed herein avoids the inherent risks of working with hydrogen.

The conversion of graphene precursor to graphene takes place on a catalyst. In this instance, the catalyst is in the form of a metal foil having a thickness between about 0.01 mm and about 1.0 mm. More typically, the metal foil may have a thickness between about 0.05 mm and 0.5 mm. The use of the foil will ensure better graphene coverage and growth with the resulting graphene in the form of graphene sheets on the metal foil. Thus, the conversion process does not produce graphene nanoparticles. Suitable metals for use in the process may include iron, cobalt, nickel, copper, molybdenum, platinum, gold, manganese, molybdenum, rhodium, titanium, tungsten and alloys. In lab scale testing the metal foil will typically be placed in a porcelain boat. However, in commercial operations other supports for the metal foil will also perform satisfactorily with the primary goal being retention of the graphene precursor on the metal foil. One criterion for a suitable support for the metal foil is that it does not participate in the reaction.

The graphene precursor is distributed over the metal foil at a depth sufficient to cover the foil. Typically, the depth of the graphene precursor will range from about 0.1 to about 5 mm. In general, efficient formation of graphene will result when using a graphene precursor depth of about 1 mm to about 2 mm. The foil with the graphene precursor on its surface is placed in the furnace, e.g. in a reactor such as a quartz tube, and the temperature within the furnace is increased at a rate of about 5° C./min. to about 10° C./min to a first target temperature between about 750° C. and about 1200° C. Typically, the first target temperature is between about 900° C. and 1000° C. The target temperature within the furnace is maintained for a period of about 30 minutes to about two hours. During the heating process, the non-reactive gas flows through the reaction chamber and over the graphene precursor at a rate of about 25 mL/hour to about 100 mL/hour. The non-reactive gas also aids in removal of evolving gaseous products such as $CO_2$, CO, $H_2O$.

Upon completion of the heating step, the furnace is cooled at a rate of about 1° C./min to about 100° C./min to a second target temperature between about 400° C. and about 800° C. Cooling of the furnace and reaction chamber may be achieved by any convenient means. The controlled cooling of the furnace and in turn the cooling of the reaction chamber is necessary for the formation of the desired graphene structure. As noted above, the resulting graphene forms on the surface of the metal foil. As noted above, the resulting graphene has three to five layers on the surface of the metal foil.

Following cooling to the second targeted temperature of about 400° C. to about 800° C., the reactor, e.g. the quartz tube, within the furnace may be rapidly cooled to room temperature. Typically, the furnace will be opened allowing exposure of the reactor to ambient conditions. The second target temperature during the cooling step will vary with the type of foil catalyst material. For iron, the second target temperature will be about 700° C. and about 800° C. and the cooling rate will be 1° C./min. to about 20° C./min. More typically, the cooling rate will be about 5° C./min to about 20° C./min. For cobalt, the target cool down temperature will be about 400° C. to about 800° C. and the cooling rate will be 1° C./min. to about 100° C./min. Typically, for a cobalt foil the cooling rate may range from about 50° C./min. to about 100° C./min. As discussed above, upon reaching the target cool down temperature, the reactor may be exposed to ambient conditions to permit rapid cooling to room temperature while nitrogen is still flowing through the reaction chamber. The reactor may also be cooled from outside by blowing air at ambient temperature to achieve the desired cooling rate.

The foregoing discussion focused on the method of converting biomass to a graphene precursor. As known to those skilled in the art, coal is a solid hydrocarbon obtained directly from nature. Biocoal and coal have similar elemental compositions. Therefore, the foregoing method for converting a graphene precursor prepared from biomass or biocoal to graphene may also be used to convert conventional coal into graphene. Coals suitable for use in the disclosed method have mass weight percentages of carbon, oxygen and hydrogen in the following ranges: C: 40-95%, O: 2-50%, Hydrogen: 3-10%. When using coal as the graphene precursor, the carbonization steps will be omitted. Thus, the method of using coal as the graphene precursor may begin with removal of any oils and continue as outlined above. As outlined above, the optional acid wash step may also be desired depending on the source and nature of the selected coal.

FIGS. 3 to 8 demonstrate the successful generation of graphene layers on iron and cobalt foils from cellulose and lignin graphene precursor.

The following examples demonstrate the successful conversion of biomass to graphene precursor and then to graphene as well as the direct conversion of coal to graphene. These examples reflect the use of cellulose and lignin which are biomass model compounds as well as woodchips (biomass) and peat coal. For each form of biomass, the following lab scale process was used.

An 81 mL MS-19 batch reactor, manufactured by HiP, was used for hydrothermal carbonization of biomass model compounds. The reactor was connected to two pressure gauges (P1 and P2) and thermocouple T1 manufactured by Omega as shown in FIG. 1. The pressure gauge P2 measured pressure up to 69 MPa while P1 can measure pressure up to 4 MPa. The lower least count of P1 helped to accurately measure the initial and the final pressures of the reactor which are below 4.0 MPa. P1 was disabled when pressure in the reactor went above 2.0 MPa. The thermocouple T1 was factory calibrated with an accuracy of $0.1°$ C. and it was connected to an external temperature display.

The step of converting the graphene precursor to graphene was carried out using several different catalytic metal foils. Specifically, the following foil materials were used: Fe and Co. To grow graphene on foils, a meter-long quartz tube was used with an inner diameter of 22 mm. The reactor and quartz tube were heated using an electric tube furnace. A schematic of the reactor and quartz tube is provided in FIG. 1.

Five grams of biomass model compound was dried at $105°$ C. and mixed with 35 mL distilled water and poured into the reactor. For the hydrothermal carbonization step, the reactor was heated at approximately $7°$ C. per minute up to $300°$ C. for a reaction time of 30 minutes. A stainless-steel frit (pore diameter 10 m) was placed at the reactor outlet to prevent the graphene precursor from clogging the tubes connecting the pressure gauges. After the reaction, the reactor was cooled by quenching it with air until it reached the room temperature ($25°$ C.) and the residual gas was vented out. The aqueous biocrude, which is the water-soluble portion of the biocrude, was poured out and graphene precursor was rinsed with acetone and dried at $110°$ C. overnight. The graphene precursor was then refluxed in 0.1 N $HNO_3$ acid overnight to remove ash and residual biocrude. After reflux, the graphene precursor was cleaned with de-ionized water at least 3 times and dried in a convection oven at $110°$ C. for 24 hours.

The conversion of the resulting graphene precursor to graphene utilized 1 cm by 1 cm metal foil. The graphene precursor was ground to a particle size of 80 mesh or less and a 1 mm layer of graphene precursor placed on the metal foil. With reference to FIG. 1, the foil and graphene precursor were heated using an electric tube furnace in a quartz tube with a continuous flow of $N_2$ at 75 mL/hr and heated to $800°$ C., $900°$ C. and $1000°$ C. for 2 hours at $5°$ C./min. The foil was then cooled to $500°$ C. and then quenched with air to cool it down to room temperature. Using the same experimental setup as described above, multilayer graphene was prepared from peat coal on a cobalt foil and multilayer graphene was prepared from biocoal obtained from woodchip on a cobalt foil. The biocoal was produced by hydrothermal carbonization at $300°$ C. and the resulting graphene precursor of 80 mesh or less was placed on the cobalt foil and heated to $1000°$ C. for 2 hours at $5°$ C./min.

The XRD analyses of the foils before and after the growth of graphene are shown in FIG. 2. FIGS. 2A-D depict the XRD analysis of Fe and Co foils respectively after heating at $700°$ C., $800°$ C., $900°$ C. and $1000°$ C. with cellulose and lignin graphene precursor. The scans at $700°$ C. reflect the lack of formation of graphene at this temperature while the scans at the higher temperatures evidence the formation of graphene. In the case of iron, three distinct peaks at approximately $45°$, $65°$ and $82°$ were observed. These peaks correspond to the α-Fe phase. Between $37°$ and $50°$, which is also known as "carbide domain", various $Fe_3C$ (cementite) peaks were observed for both cellulose and lignin graphene precursor heated with Fe at $900°$ C. and $1000°$ C.

Figure 2A:
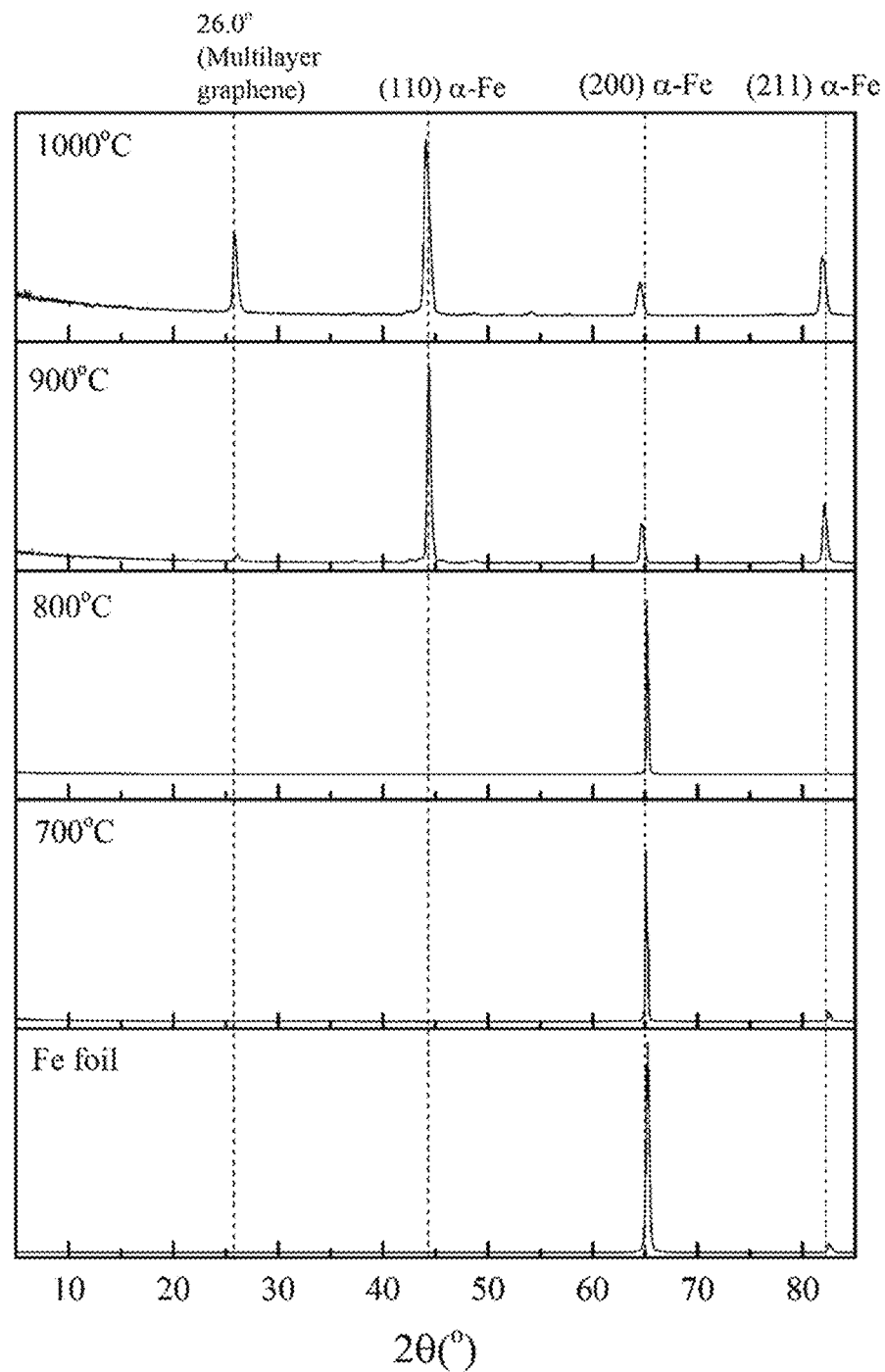
FIGS. 2A-2D depicts X-ray diffraction analysis of the metal foils used in the process with data representative of before and after performance of the disclosed process.
Figure 2B:
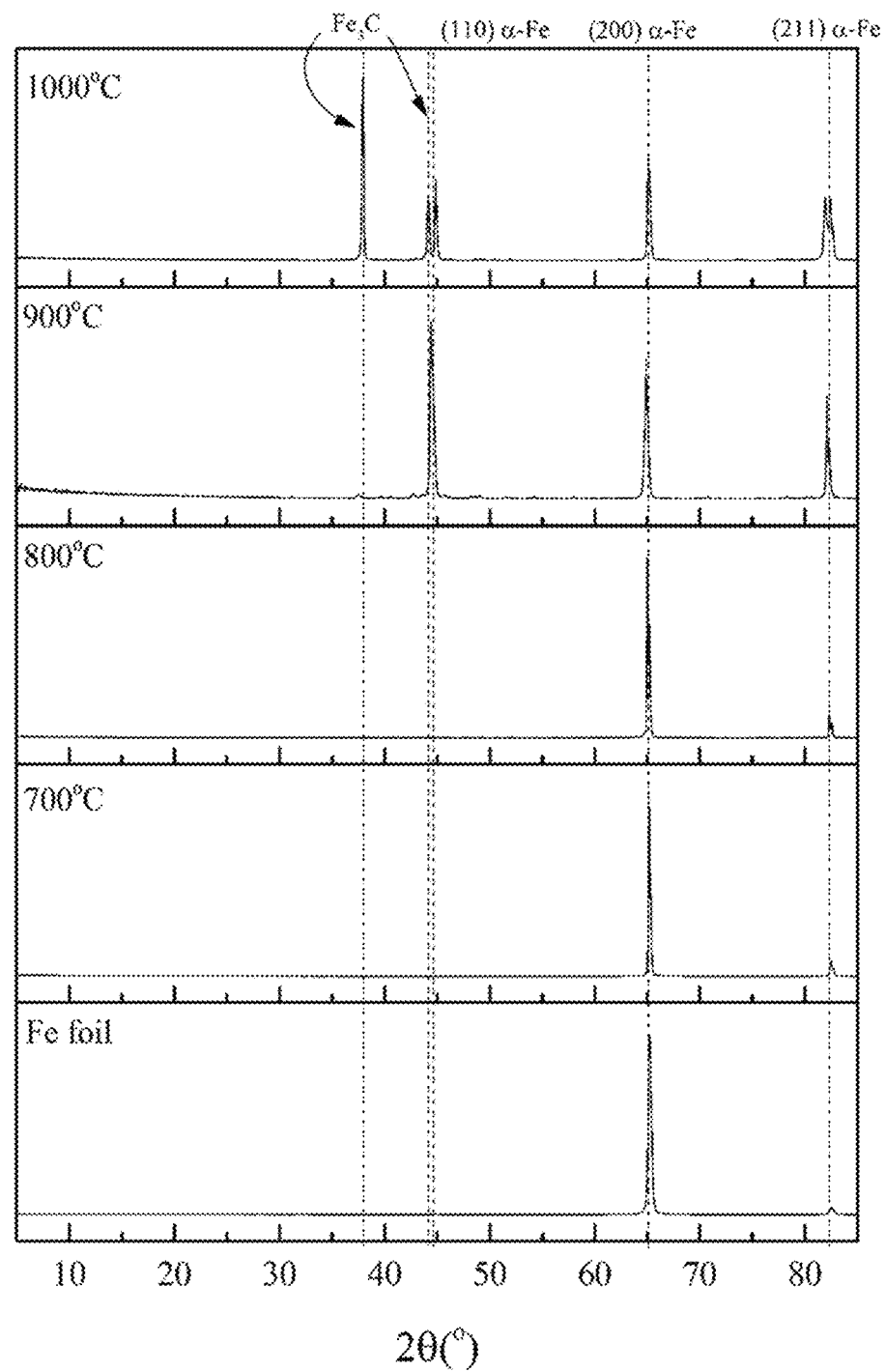
Figure 3:
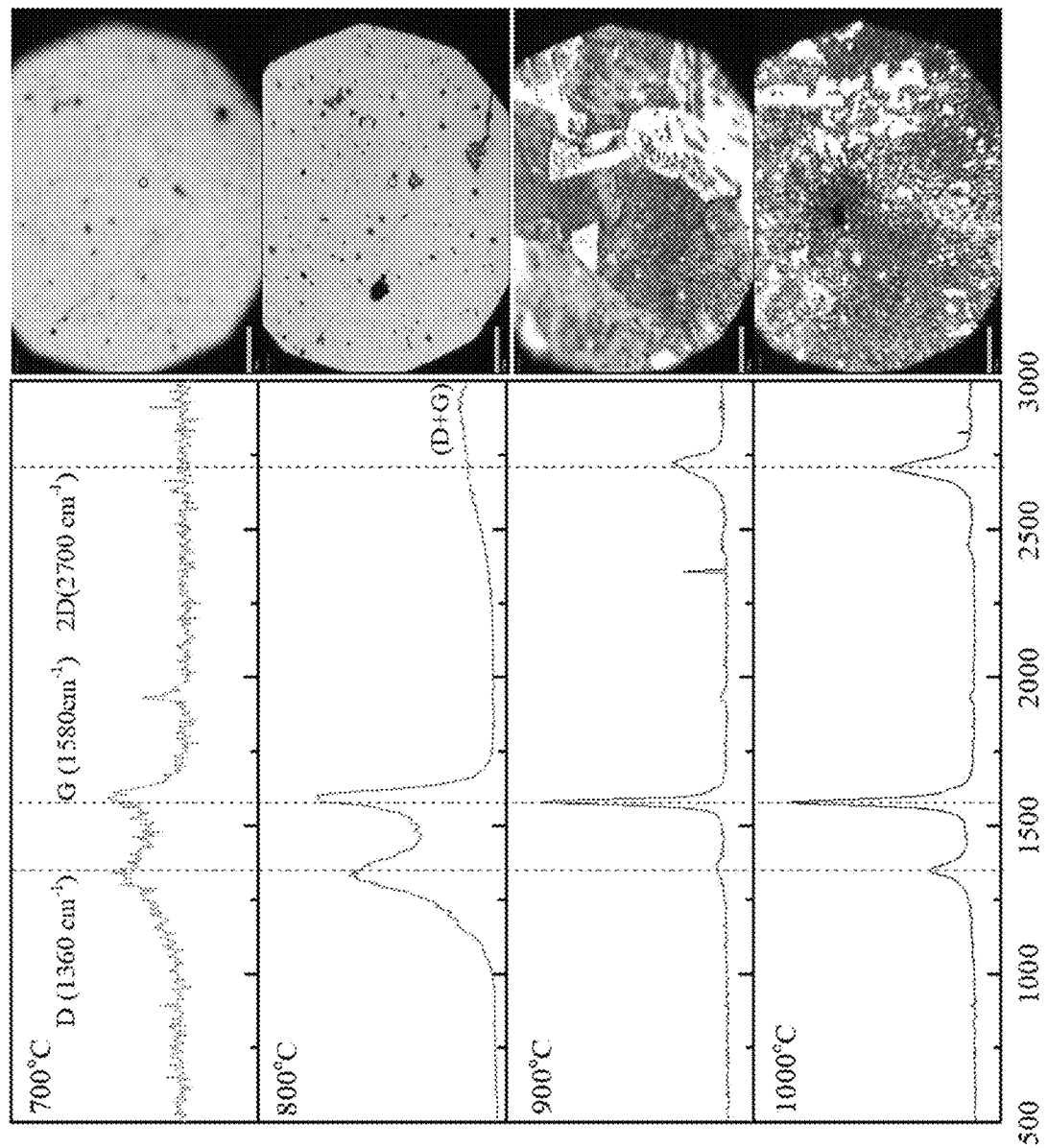
FIG. 3 depicts Raman spectroscopy of an iron foil following performance of the disclosed process at various temperatures with cellulose biomass as the starting material.

With reference to FIG. 3, the Raman spectroscopy demonstrates the presence of graphene in the case of cellulose graphene precursor heated with Fe at $900°$ C. and $1000°$ C. The X-Ray diffractogram of FIG. 2A shows the presence of highly crystalline 3-5 layer graphene which is represented by the peak at $26°$.

FIGS. 12A-C and 13A-C depict the XPS spectra of Fe and Co foil, respectively with cellulose graphene precursor on the respective foil. The spectra shows the presence of C1S peaks confirming the presence of graphene.

Figure 2C:
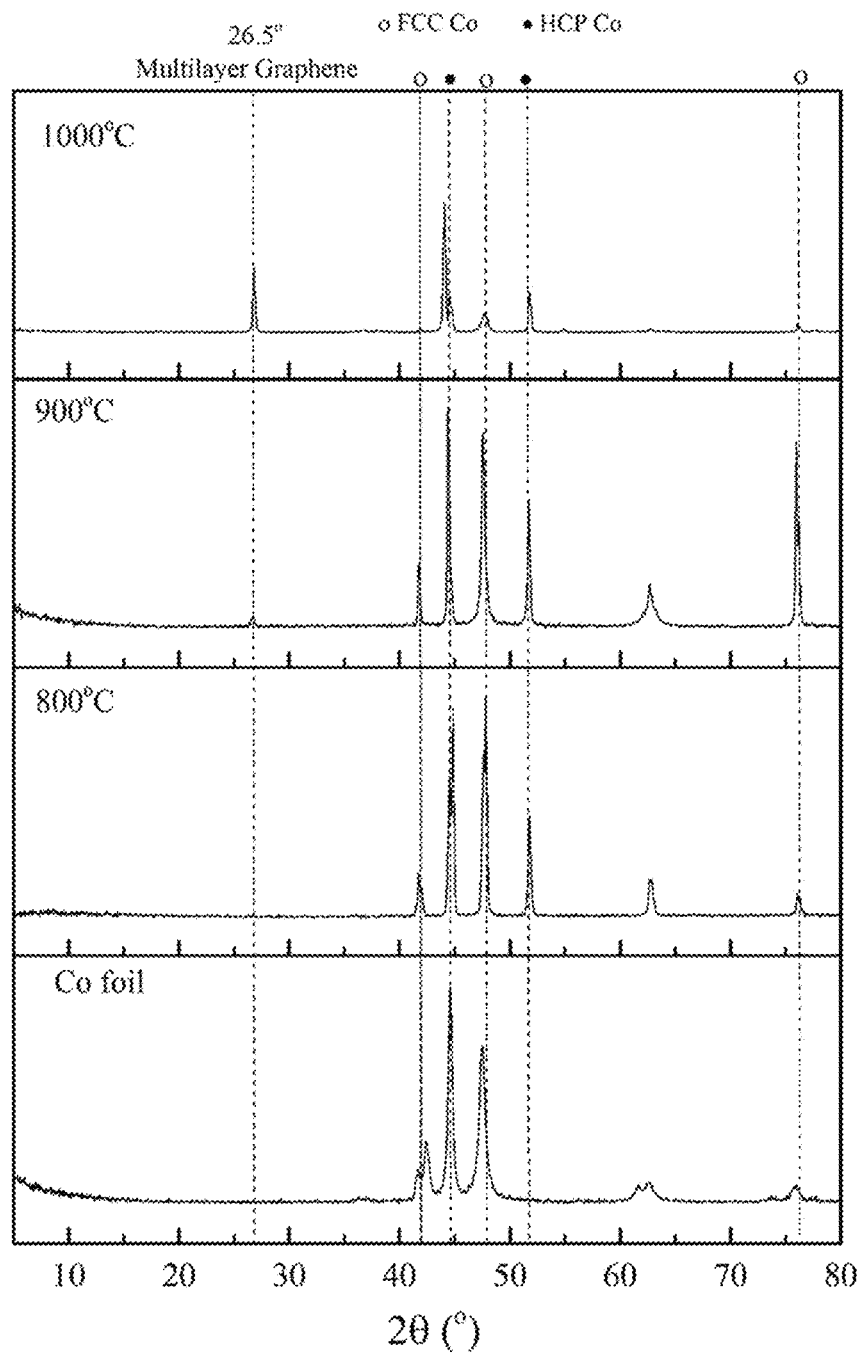
Figure 2D:
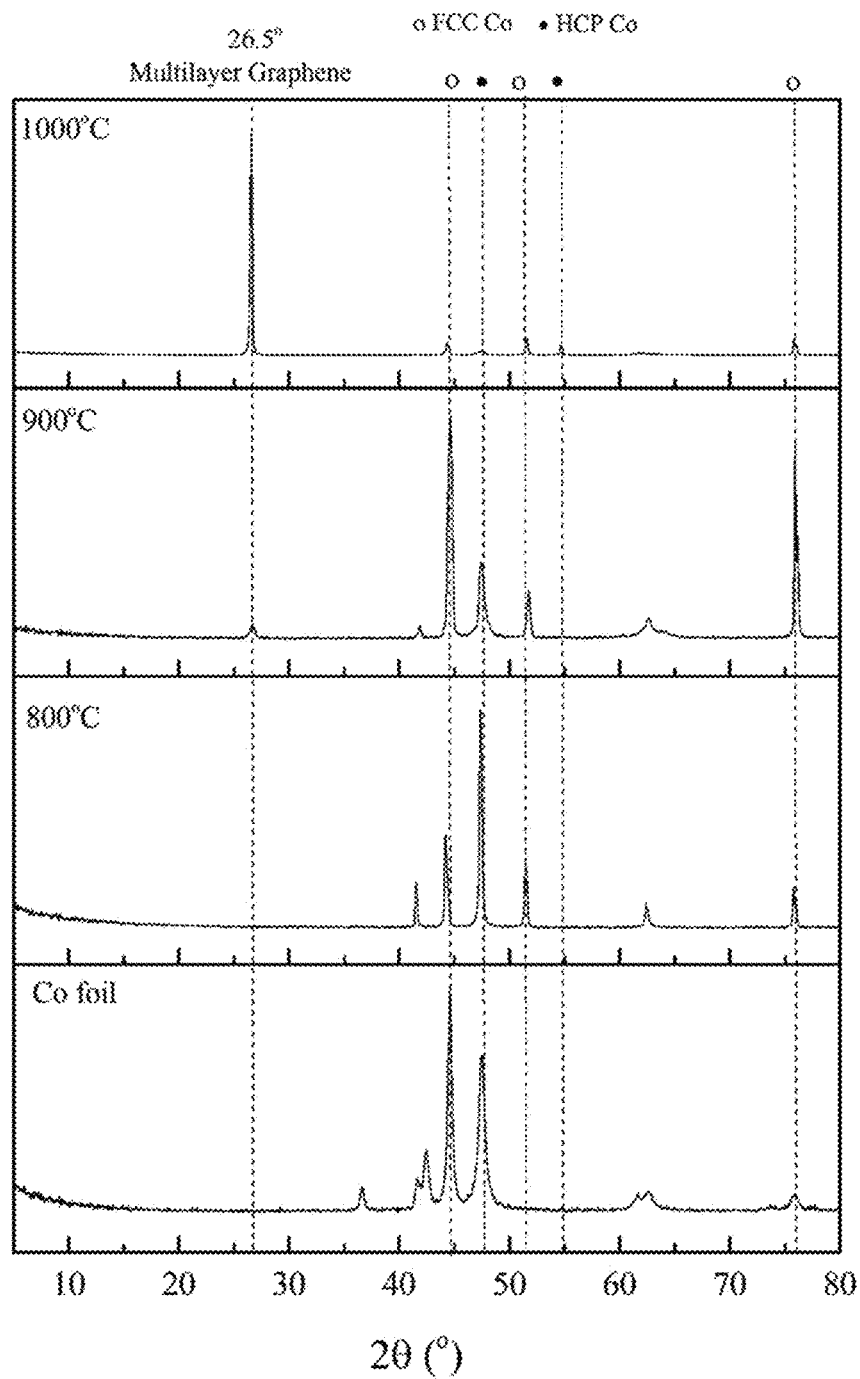
Figure 8:
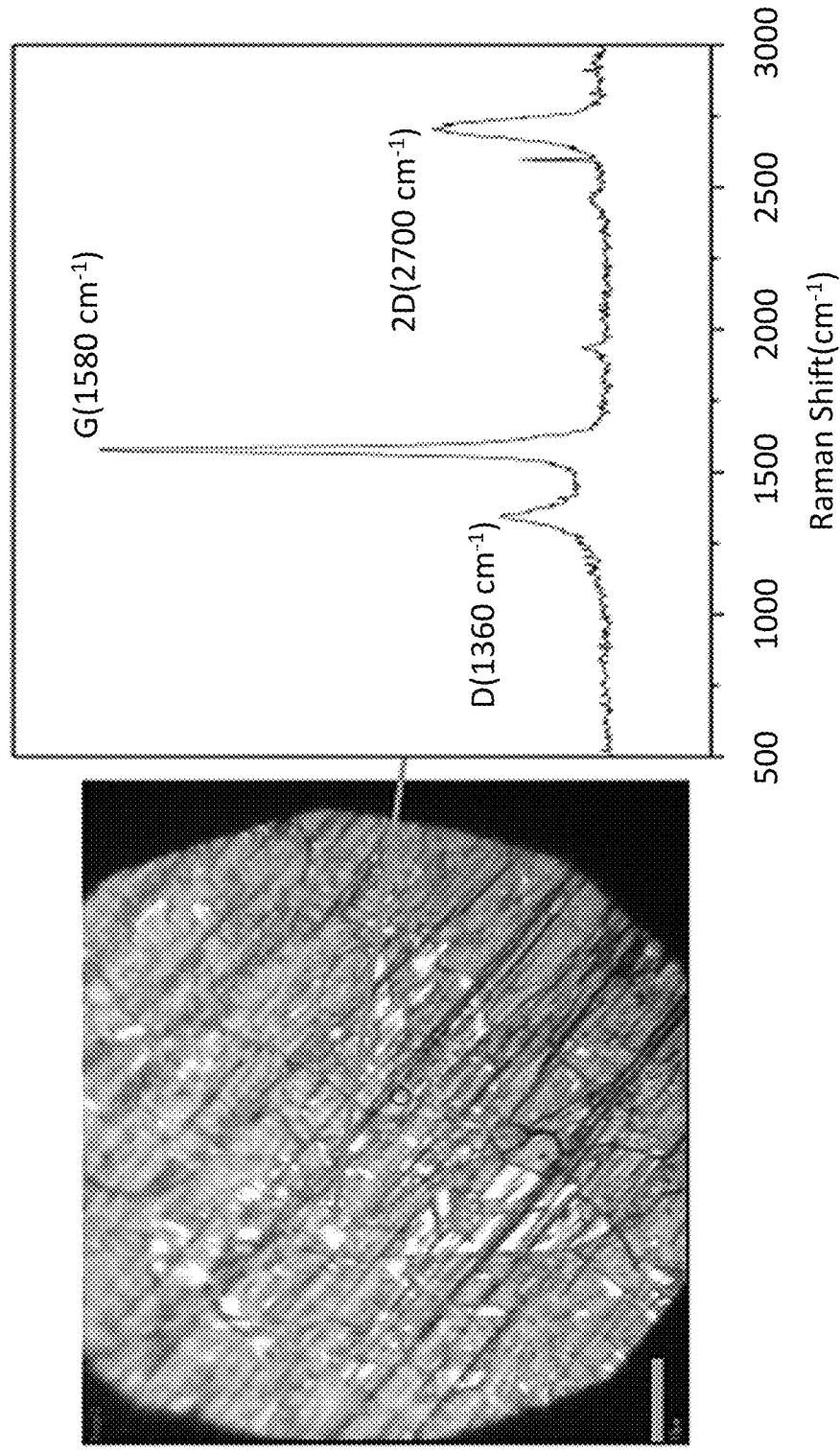
FIG. 8 depicts the Raman Spectrum of multi-layer graphene on Co foil heated with cellulose graphene precursor at 1000° C.

FIGS. 2C and 2D show the XRD analysis of Co foil heated with cellulose and lignin graphene precursor respectively. Unlike Fe, no carbide peaks were observed as carbides of cobalt are not stable at room temperature. For cellulose and lignin graphene precursors heated with Co at 900 and $1000°$ C., peak at around $26.5°$ which signifies the presence of highly crystalline multilayer graphene. As shown in FIG. 8, Raman analysis at different points on the foil confirmed the presence of multilayer graphene on the surface of the foil.

With reference to FIGS. 3-6, Raman spectroscopy of graphene on Fe and Co foils are depicted. Raman Spectroscopy has been widely used in literature to characterize the quality of graphene using a 514 nm excitation laser. There are 3 distinct peaks that are generally observed in the Raman spectrum of graphene. A peak at 1370 $cm^{-1}$, also known as the D peak, signifies the presence of defects. The G and 2D peaks at 1580 $cm^{-1}$ and 2700 $cm^{-1}$ represent the optical phonon mode of interlayer carbon atoms and the second harmonic band respectively.

As depicted in FIG. 3, the aforementioned three peaks are visible for cellulose graphene precursor heated at $900°$ C. and $1000°$ C. The intensity of D peak of the Raman spectrum at $900°$ C. and $1000°$ C. signifies the presence of minimal defects. The 2D/G ratio, which is the ratio of intensities of 2D and G peaks, were less than one in both the cases, which indicates the presence of multilayer graphene. As the number of layers of graphene increase, 2D/G decreases. In the case of graphene prepared at $900°$ C. and $1000°$ C., the 2D/G ratios were 0.28 and 0.45 respectively. The D and the G peaks were located at 1360 $cm^{-1}$ and 1580 $cm^{-1}$ respectively while the 2D peak was observed at 2700 $cm^{-1}$. In the case of cellulose graphene precursor heated with Fe at $800°$ C., no distinct 2D peaks were observed and the D and G peaks overlapped. This is due to presence of disordered graphene where instead of the distinct 2D peak, a broadened D+G with smeared with the 2D peak.

Figure 4:
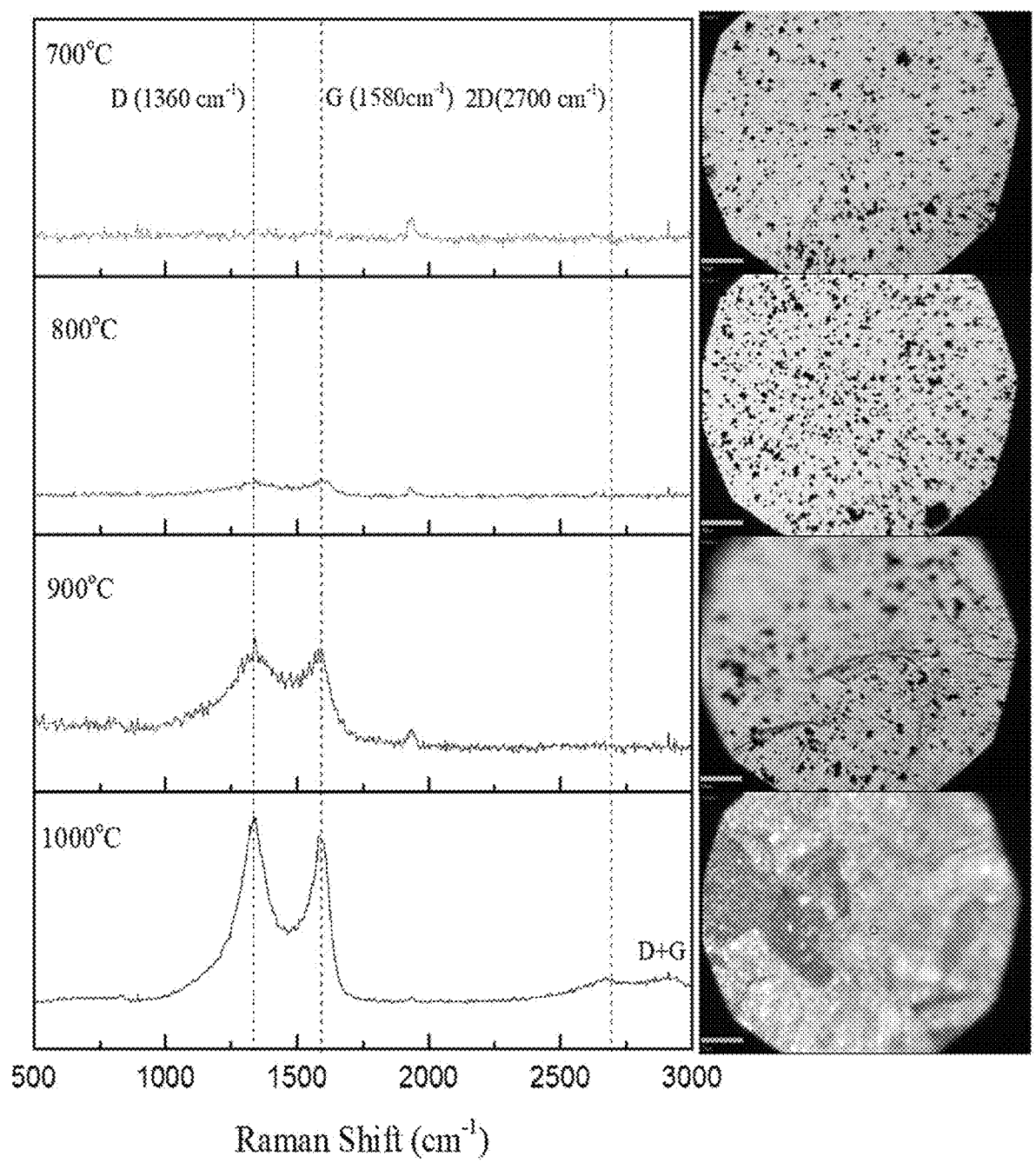
FIG. 4 depicts Raman spectroscopy of an iron foil following performance of the disclosed process at various temperatures with lignin biomass as the starting material.
Figure 9:
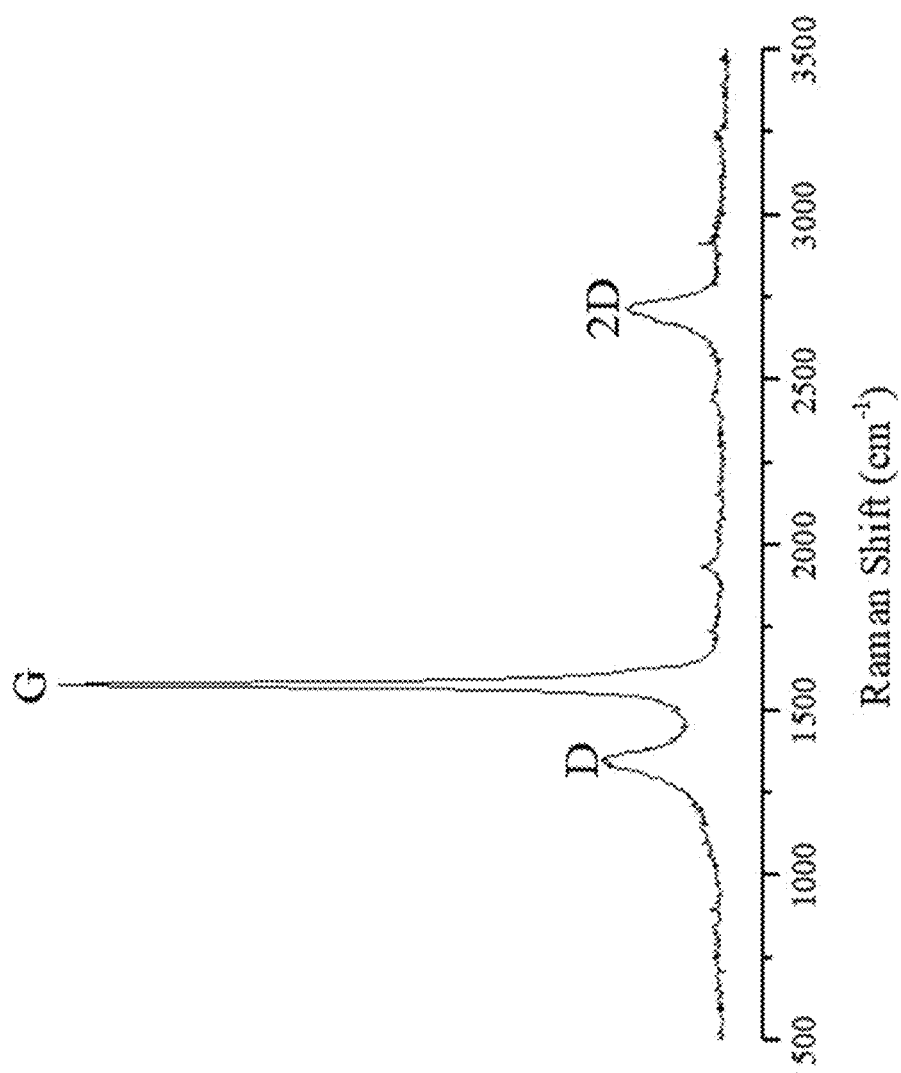
FIG. 9 depicts the Raman Spectrum of graphene prepared from lignin biocoal on Fe foil after synthetization at 1000° C. and cooled at 10° C./min.
Figure 10:
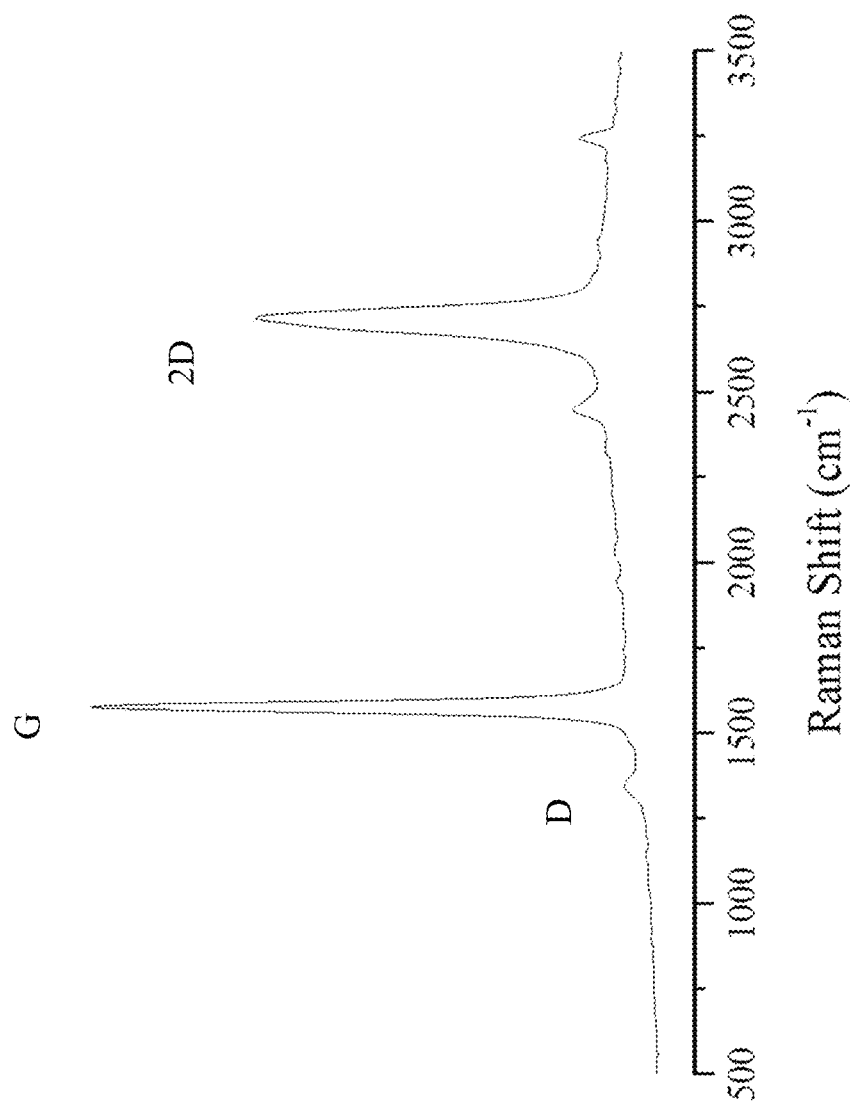
FIG. 10 depicts the Raman Spectrum of graphene synthesized from peat coal on Co foil.
Figure 11:
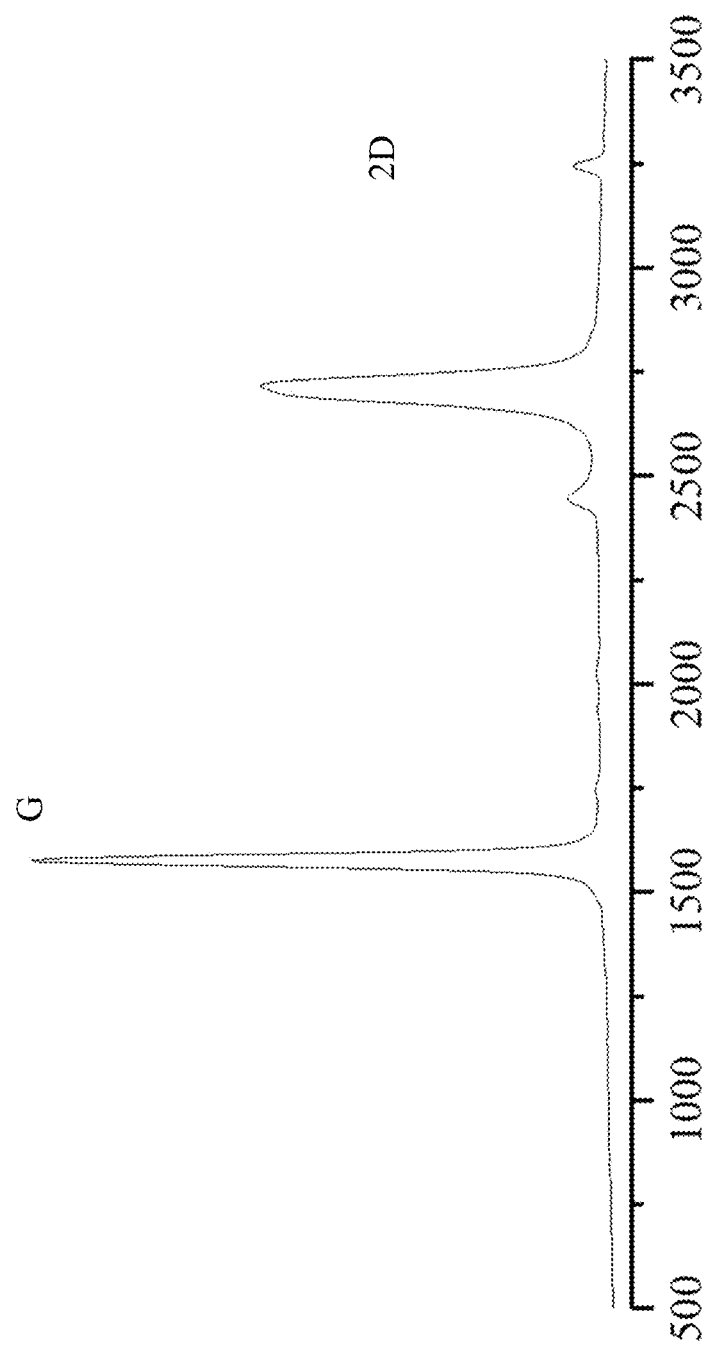
FIG. 11 depicts the Raman Spectrum of graphene synthesized from biocoal (prepared from woodchips) on Co foil.
Figure 12A:
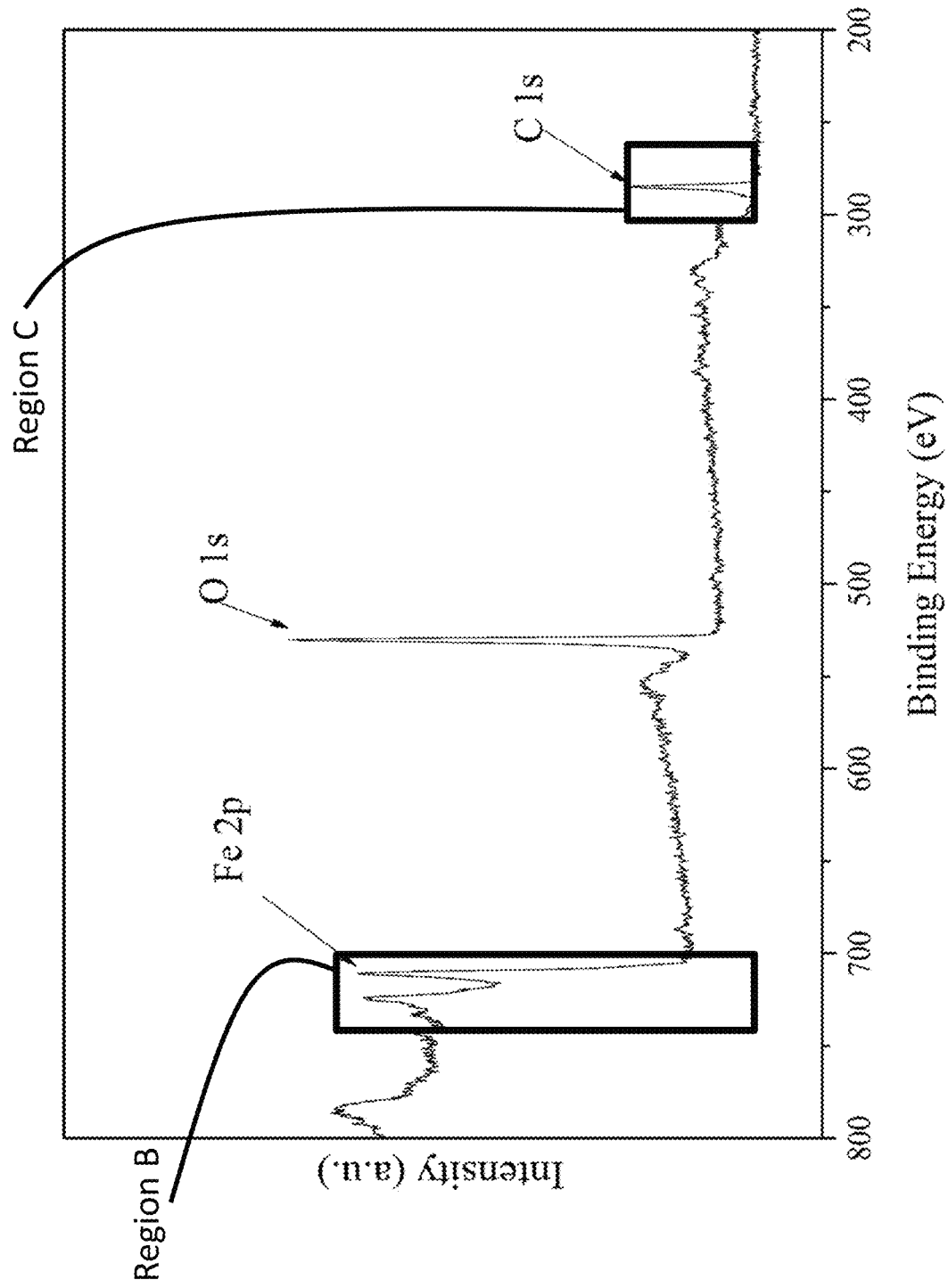
FIG. 12A provides the XPS spectra of graphene prepared from cellulose graphene precursor on Fe foil after cooling from 1000° C. to 727° C. at a rate of 10° C./min.
Figure 12B:
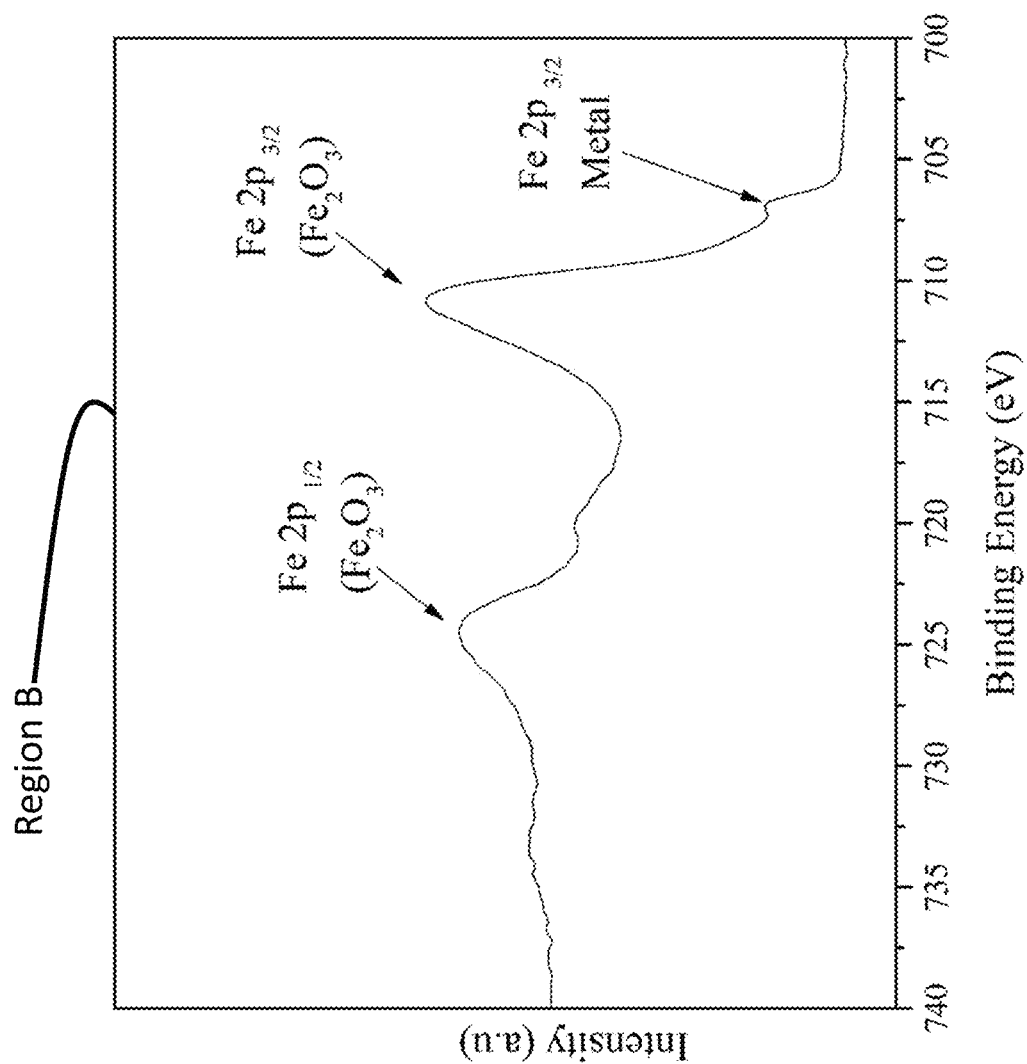
FIG. 12B provides a detailed view of region B in FIG. 12A.
Figure 12C:
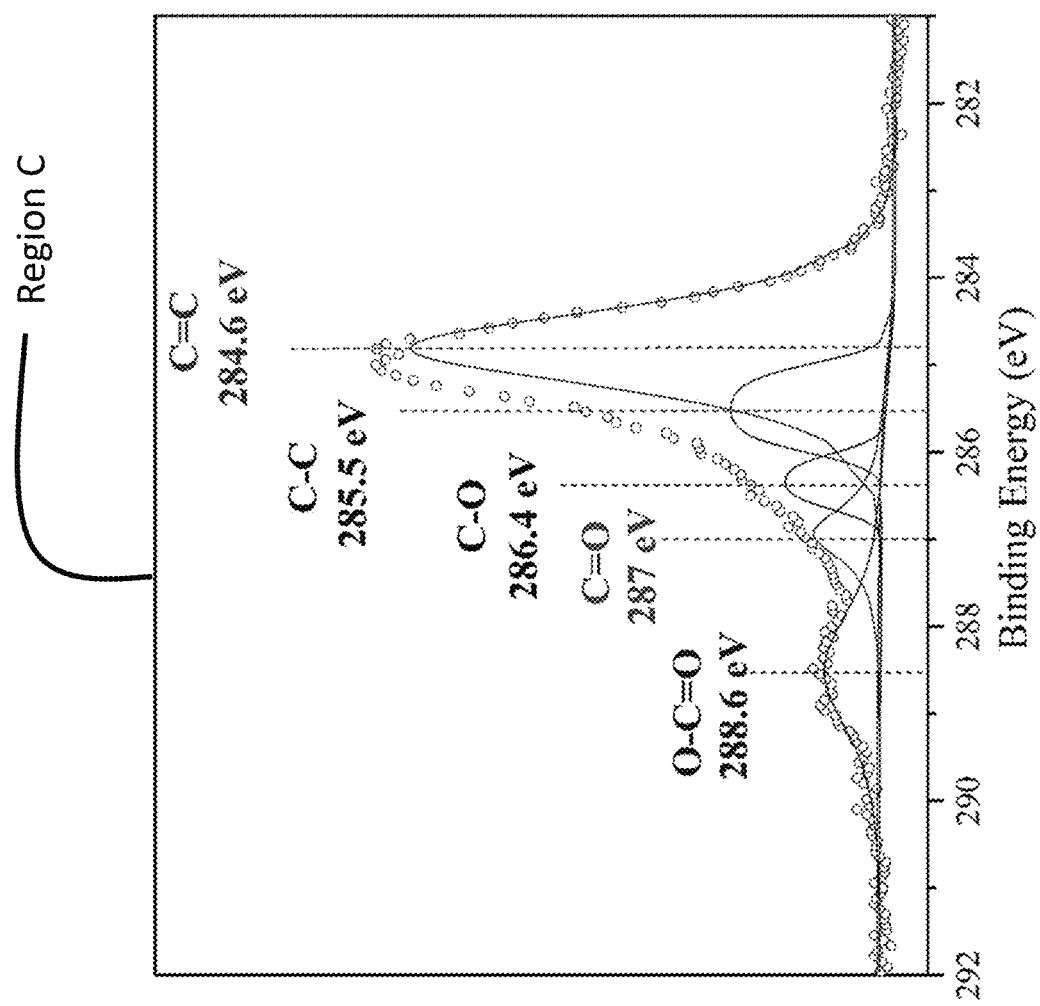
FIG. 12C provides a detailed view of region C in FIG. 12A.
Figure 13A:
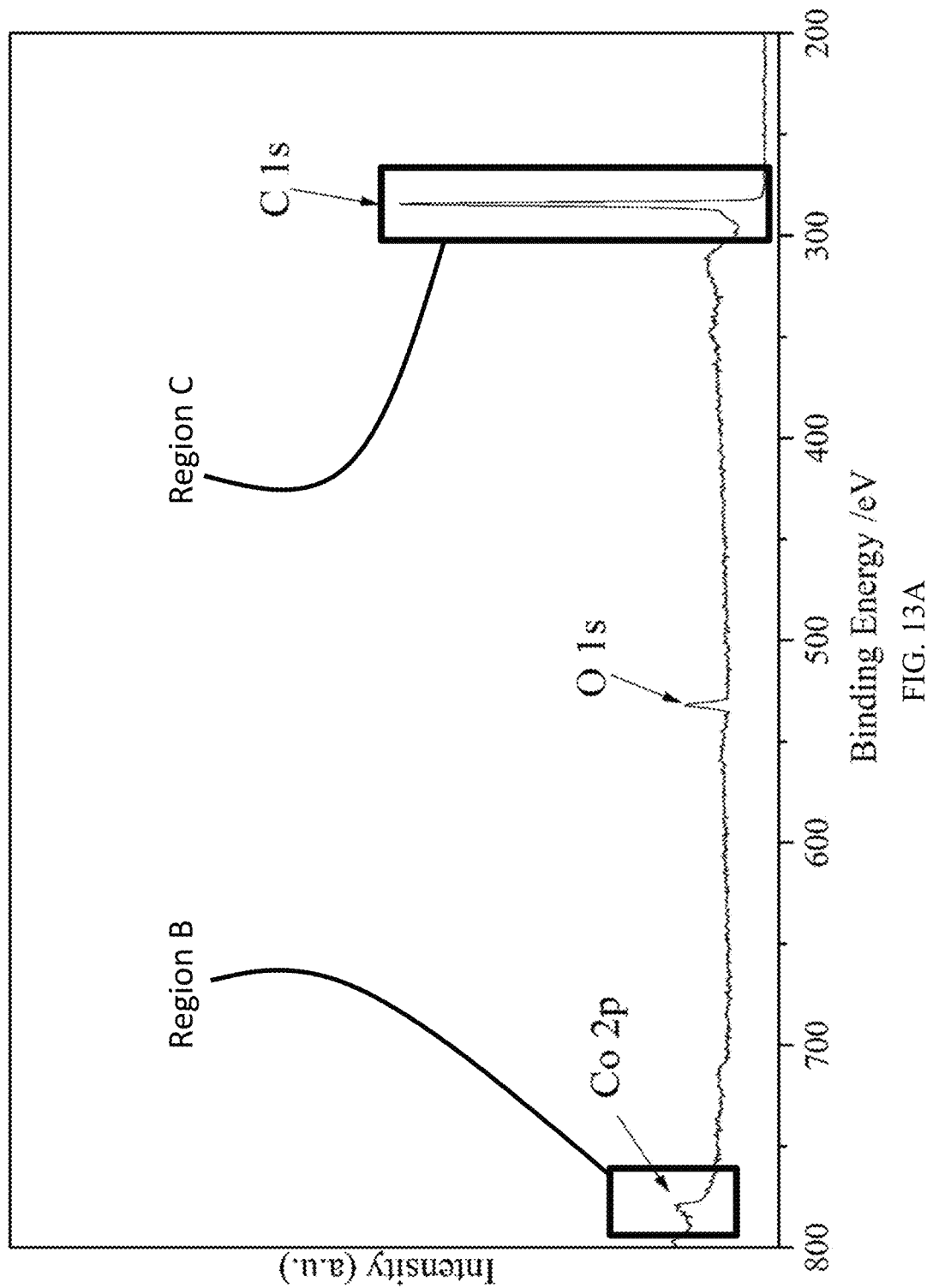
FIG. 13A provides the XPS spectra of graphene prepared from cellulose graphene precursor on Co foil after instantaneous cooling by quenching with air from 1000° C. to ambient temperature.
Figure 13B:
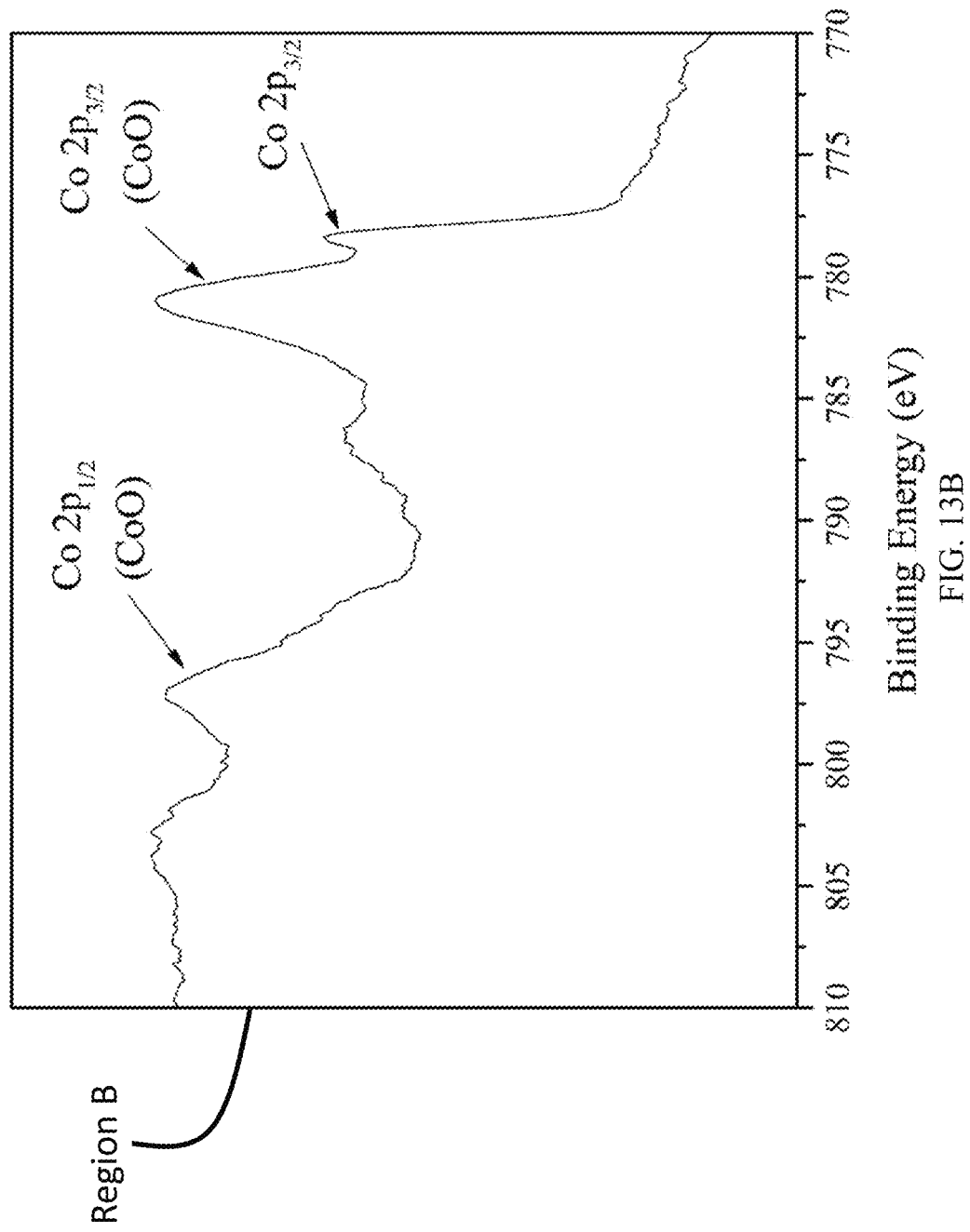
FIG. 13B provides a detailed view of region B in FIG. 13A.
Figure 13C:
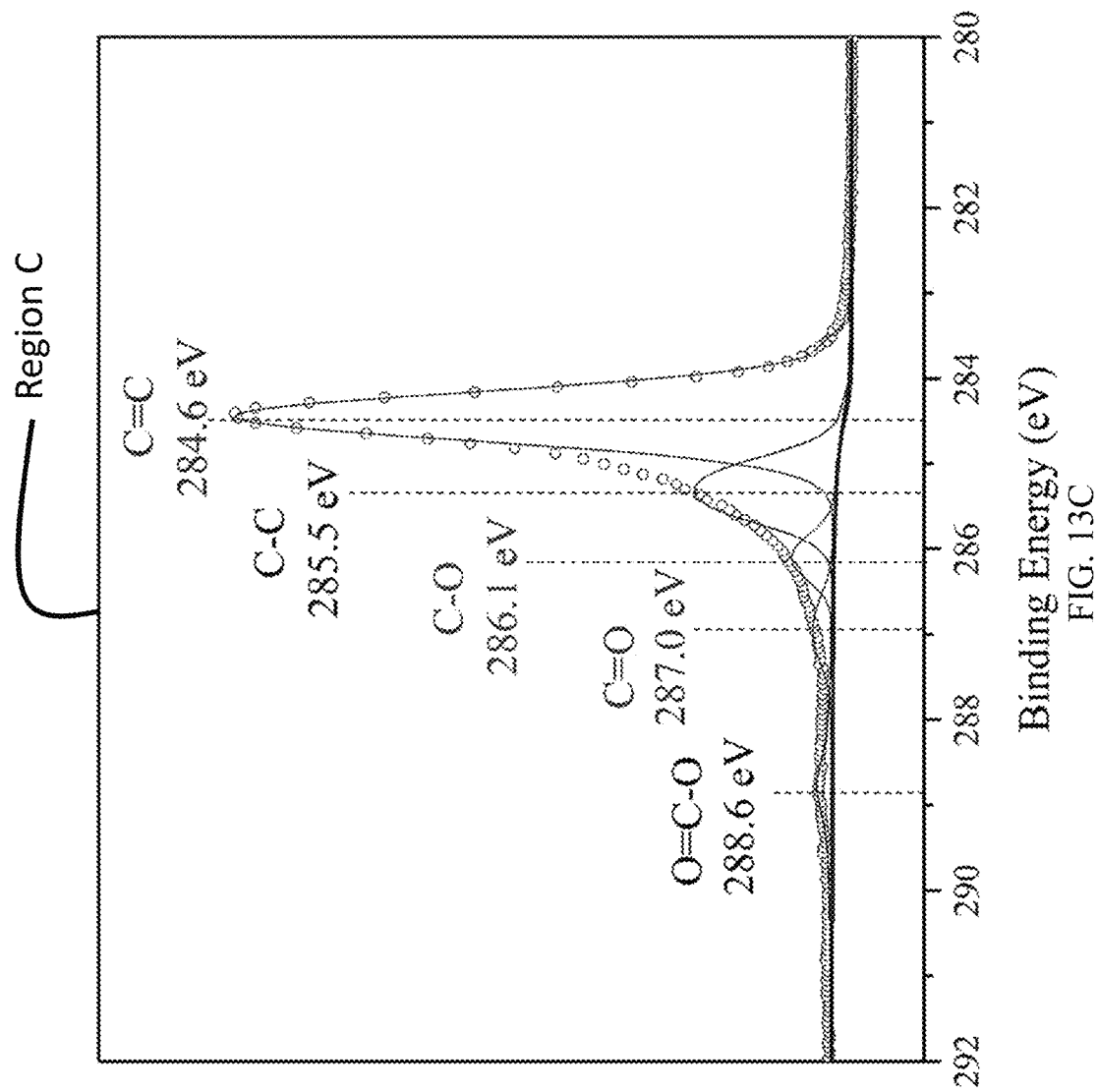
FIG. 13C provides a detailed view of region C in FIG. 13A.

With reference to FIG. 4, only disordered graphene was observed in the case of lignin graphene precursor at $900°$ C. and $1000°$ C. on Fe foil. The Raman spectra of disordered graphene from lignin graphene precursor is shown in FIG. 4. The G and D peaks merged together and the 2D peak was smeared with D+G for graphene grown at $1000°$ C. At $900°$ C., no peaks were observed near 2700 $cm^{-1}$. However, at $800°$ C. and $700°$ C., D, G and 2D peaks were not detected and this signifies the absence of graphene. The images in FIGS. 3 and 4 from the optical microscope on the Raman instrument shows the presence of graphene flakes for cellulose graphene precursor heated with Fe at 900° C. and 1000° C. and lignin graphene precursor heated at 1000° C. while residual graphene precursor particles are seen the other foils. As discussed above, the production of ordered graphene from lignin graphene precursor on iron foil requires a different cooling rate as evidenced by FIG. 9. The cooling rate for depositing graphene on iron when using lignin graphene precursor is about 1° C./min to about 10° C./min. FIG. 9 shows the Raman spectrum of graphene on Fe obtained from biocoal. The biocoal graphene precursor was placed on the Fe foil and heated to 1000° C. for 2 hours and cooled at 10° C./min to produce graphene. The 2D/G ratio was found to be 0.3 which indicate the presence of 3-5 layer graphene. The intensity of D peak of the Raman spectrum signifies the presence of minimal defects.

Figure 5:
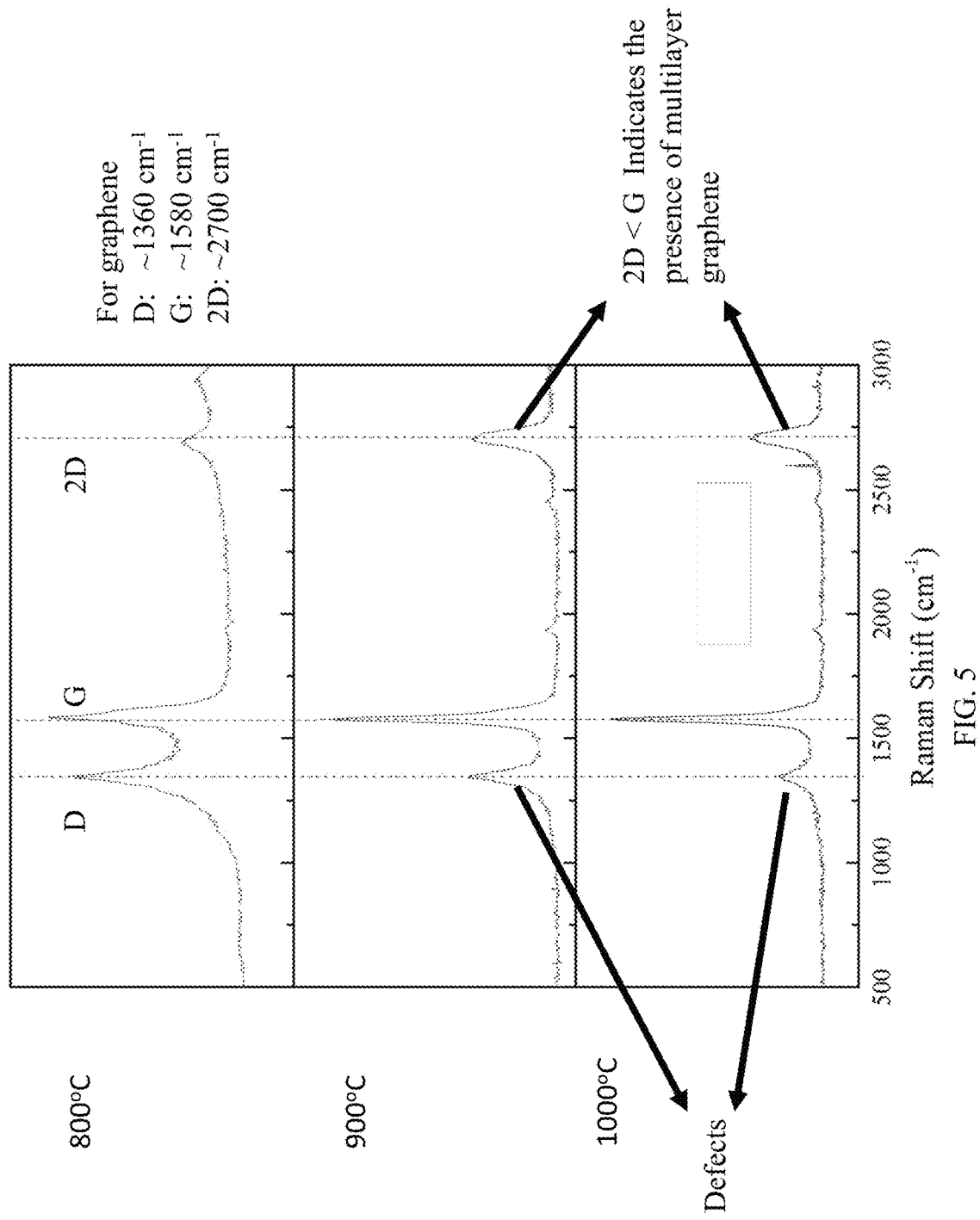
FIG. 5 depicts Raman spectroscopy of a cobalt foil following performance of the disclosed process at various temperatures with cellulose biomass as the starting material.
Figure 6:
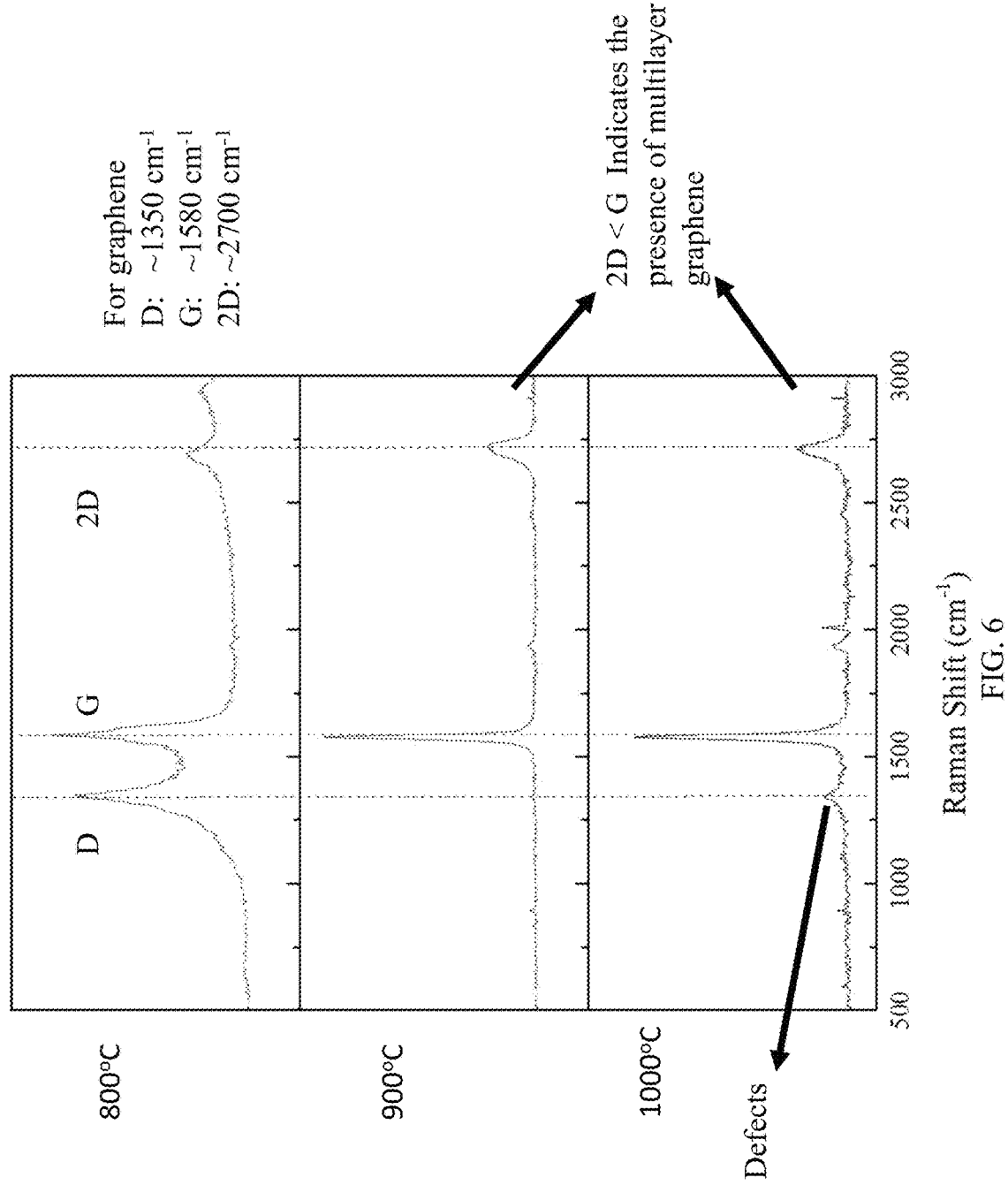
FIG. 6 depicts Raman spectroscopy of a cobalt foil following performance of the disclosed process at various temperatures with lignin biomass as the starting material.

Turning now to FIG. 5, thermally treated Co with graphene precursor at 900° C. and 1000° C. formed multilayer graphene on both sides of the foil (unlike Fe where graphene formed on one side only). As shown in FIGS. 5 and 6, multilayer graphene was detected from both cellulose and lignin graphene precursor. The 2D/G ratio for cellulose and lignin graphene precursor at 1000° C. and 900° C. were 0.67 and 0.52, and 0.27 and 0.23 respectively. However, XRD results for Co foils heated with cellulose and lignin graphene precursor at 900° C. and 1000° C. also indicated the presence of highly crystalline multilayer graphene.

Figure 7:
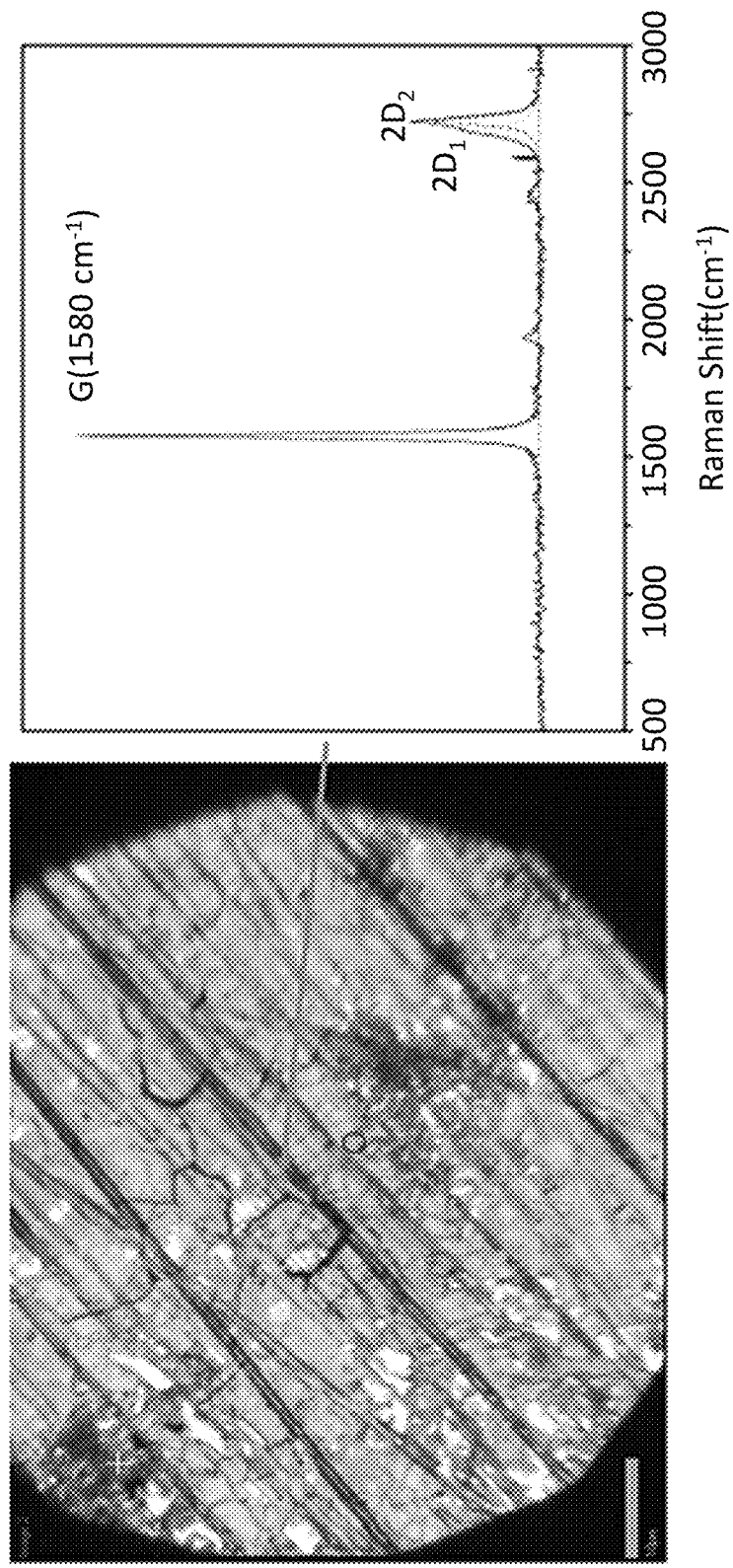
FIG. 7 depicts the Raman Spectrum of graphite on Co foil heated with cellulose graphene precursor at 1000° C. The $2D_1$ and $2D_2$ peaks are shown in green and blue dashed lines respectively and they were obtained by Lorentzian deconvolution.

As an example, FIGS. 7 and 8 depict the Raman spectroscopy analysis of two different random points on the Co foil heated with cellulose graphene precursor at 1000° C. FIG. 7 shows the presence of graphite with its characteristic $2D_1$ and $2D_2$ peaks around 2700 cm$^{-1}$. FIG. 8 shows the presence of multilayer graphene at another point on the same foil with a distinct 2D peak. As seen in FIGS. 5 and 6, the D and G peaks were merged together and the 2D peak was smeared with the D+G peak.

Thus, the foregoing examples demonstrate the ability to produced ordered graphene in a plurality of layers on the surface of a catalyst where the catalyst is in the form of a metal foil. Additionally, the examples demonstrate the ability to produce graphene in the absence of hydrogen and without the need for vacuum operational conditions.

Other embodiments of the present invention will be apparent to one skilled in the art. As such, the foregoing description merely enables and describes the general uses and methods of the present invention. Accordingly, the following claims define the true scope of the present invention.

What is claimed is:

1. A method of preparing graphene on a catalyst in the form of a metal foil surface comprising:
    providing a graphene precursor having carbon, oxygen and hydrogen weight percentages in the following ranges: C: 40-95%, O: 15-50%, Hydrogen: 3-10%;
    dry the graphene precursor at a temperature between about 100° C. and about 110° C. for a period of about 12 hours to about 24 hours;
    reducing the particle size of the graphene precursor;
    placing the graphene precursor on a surface of a metal foil and placing the metal foil with the graphene precursor in a reactor;
    flowing a gas that is non-reactive with the graphene precursor through the reactor;
    increasing the temperature within the reactor to a first target temperature between about 750° C. and about 1200° C.;
    maintaining the target temperature for about 30 minutes to about 120 minutes;
    cooling the catalyst metal foil within the reactor at a rate of about 1° C./min to about 100° C./min to a second target temperature between about 400° C. and about 800° C.; and,
    upon reaching the second target temperature within the reactor, rapidly cooling the catalyst metal foil within the reactor to ambient conditions by exposing the catalyst metal foil to ambient conditions while maintaining flow of said gas;
    thereby providing layered graphene on the surface of the metal foil.

2. The method of claim 1, prior to the drying step, further comprising the step of washing the graphene precursor with a solvent suitable for removing soluble oils from said graphene precursor.

3. The method of claim 2, wherein the step of washing the graphene precursor with a solvent suitable for removing soluble oils from said graphene precursor uses about 75 ml of solvent to about 100 ml of solvent per gram of graphene precursor.

4. The method of claim 2, wherein the solvent suitable for removing soluble oils from the graphene precursor is selected from the group consisting of: acetone, methyl ethyl ketone, tetrahydrofuran.

5. The method of claim 2, prior to the drying step, further comprising the step of acid washing the graphene precursor for a period of time between about 12 hours and about 24 hours.

6. The method of claim 5, further comprising the step of neutralizing the graphene precursor by washing with water.

7. The method of claim 5, wherein the acid washing step uses about 50 ml of acid to about 150 ml of acid per gram of graphene precursor.

8. The method of claim 1, wherein the flowing gas passes through the reactor at a rate between about 10 ml/hour and about 100 ml/hour.

9. The method of claim 1, wherein the flowing gas passes through the reactor at a space velocity between about 0.052 h$^{-1}$ and about 0.263 h$^{-1}$.

10. The method of claim 1, wherein the volume and flow rate of said flowing gas is sufficient to preclude reaction of the graphene precursor with oxygen and to remove substantially all atmospheric oxygen from the reactor.

11. The method of claim 1, wherein the volume and flow rate of said flowing gas is sufficient to maintain the reactor within 1 psi of atmospheric conditions.

12. The method of claim 1, wherein said metal foil has a thickness between about 0.01 mm and about 1.0 mm and the graphene precursor is distributed over the metal foil at a depth of about 0.1 mm to about 5 mm.

13. The method of claim 1, wherein said step of heating to a target temperature takes place by heating at a rate of about 5° C./min. to about 10° C./min.

14. The method of claim 1, wherein when said metal foil is iron, said step of cooling to said second target temperature takes place at a rate of about 5° C./min to about 20° C./min and said target temperature is between about 700° C. and about 800° C.

15. The method of claim 1, wherein when said metal foil is cobalt, said step of cooling to said second target temperature takes place at a rate of about 50° C./min to about 100° C./min and said target temperature is between about 400° C. and about 800° C.

16. The method of claim 1, wherein the step of cooling the catalyst metal foil within the reactor to ambient conditions takes place by opening the reactor and exposing the reactor to blowing air at ambient temperature.

17. The method of claim 1, wherein the step of reducing the particle size of the graphene precursor provides particle sizes less than 35 U.S. Standard Mesh.

18. The method of claim 1, wherein the step of reducing the particle size of the graphene precursor provides particle sizes less than 80 U.S. Standard Mesh.

19. The method of claim 1, wherein the step of reducing the particle size of the graphene precursor provides particle sizes less than 100 U.S. Standard Mesh.

20. A method for preparing a layered graphene on a catalyst metal foil surface comprising:
    providing a plant based source of carbon, said plant based source containing at least 20% carbon by weight;
    mixing said plant based source of carbon with water at a ratio of about one part plant based source of carbon to five parts water to about one part plant based source of carbon to ten parts water to form a mixture of plant based source of carbon in water;
    carbonizing the plant based source of carbon in water by heating the mixture of plant based source of carbon in water to a temperature between about 200° C. and about 400° C. for a period of at least 30 minutes;
    isolating the graphene precursor, said graphene precursor having carbon, oxygen and hydrogen weight percentages in the following ranges: C: 40-95%, O: 15-50%, Hydrogen: 3-10%;
    drying the graphene precursor at a temperature between about 100° C. and about 110° C. for a period of about 12 hours to about 24 hours;
    reducing the particle size of the graphene precursor;
    placing the graphene precursor on a catalyst metal foil and placing the catalyst metal foil with the graphene precursor in a reactor;
    flowing a gas that is non-reactive with the graphene precursor through the reactor;
    increasing the temperature within the reactor to a first target temperature between about 750° C. and about 1200° C.;
    maintaining the target temperature for about 30 minutes to about 120 minutes;
    cooling the catalyst metal foil within the reactor at a rate of about 1° C./min to about 100° C./min to a second target temperature between about 400° C. and about 800° C.;
    upon reaching the second target temperature, rapidly cooling the catalyst metal foil within the reactor to ambient conditions by exposing the catalyst metal foil to ambient conditions while maintaining flow of said gas;
    thereby providing layered graphene on surface of the metal foil.

21. The method of claim 20, wherein the step of carbonizing the plant based source of carbon in water takes place within a reactor and increases the temperature within the reactor to a temperature between about 200° C. and about 400° C. by heating at a rate of about 5° C./minute to about 10° C./minute.

22. The method of claim 20, wherein the step of carbonizing the plant based source of carbon in water takes place in a sealed reactor such that vaporization of water within the reactor increases the internal pressure of the reactor to a pressure between about 2 MPa to about 20 MPa.

23. The method of claim 20, wherein said plant based source of carbon is selected from the group consisting of: cellulose, hemicellulose and lignin.

24. The method of claim 20, prior to the drying step, further comprising the step of washing the graphene precursor with a solvent suitable for removing soluble oils from said graphene precursor.

25. The method of claim 20, prior to the drying step, further comprising the step of acid washing the graphene precursor for a period of time between about 12 hours and about 24 hours.

26. The method of claim 25, further comprising the step of neutralizing the graphene precursor by washing with water.

27. The method of claim 20, wherein the flowing gas passes through the reactor at a rate between about 10 ml/hour and about 100 ml/hour.

28. The method of claim 20, wherein the flowing gas passes through the reactor at a space velocity between about $0.052\ h^{-1}$ and about $0.263\ h^{-1}$.

29. The method of claim 20, wherein the volume and flow rate of said flowing gas is sufficient to preclude reaction of the graphene precursor with oxygen and to remove substantially all atmospheric oxygen from the reactor.

30. The method of claim 20, wherein said metal foil has a thickness between about 0.01 mm and about 1.0 mm and the graphene precursor is distributed over the metal foil at a depth of about 0.1 mm to about 5 mm.

31. The method of claim 20, wherein said step of heating to a target temperature takes place by heating at a rate of about 5° C./min. to about 10° C./min.

32. The method of claim 20, wherein when said metal foil is iron, said step of cooling to said second target temperature takes place at a rate of about 5° C./min to about 20° C./min and said target temperature is between about 700° C. and about 800° C.

33. The method of claim 20, wherein when said metal foil is cobalt, said step of cooling to said second target temperature takes place at a rate of about 50° C./min to about 100° C./min and said target temperature is between about 400° C. and about 800° C.

34. The method of claim 20, wherein the step of cooling the catalyst metal foil within the reactor to ambient conditions takes place by opening the reactor and exposing the reactor to blowing air at ambient temperature.

35. The method of claim 20, wherein the volume and flow rate of said flowing gas is sufficient to maintain the reactor within 1 psi of atmospheric conditions.

36. The method of claim 1, wherein said gas does not contain hydrogen or oxygen.

37. The method of claim 20, wherein said gas does not contain hydrogen or oxygen.

* * * * *